(12) United States Patent
Miura et al.

(10) Patent No.: US 8,598,535 B2
(45) Date of Patent: Dec. 3, 2013

(54) ULTRAVIOLET PROTECTION EFFECT EVALUATION METHOD, EVALUATION APPARATUS, AND RECORDING MEDIUM

(75) Inventors: Yoshimasa Miura, Kanagawa (JP); Masato Hatao, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/823,438

(22) PCT Filed: Jul. 13, 2011

(86) PCT No.: PCT/JP2011/065939
§ 371 (c)(1),
(2), (4) Date: Mar. 14, 2013

(87) PCT Pub. No.: WO2012/035864
PCT Pub. Date: Mar. 22, 2012

(65) Prior Publication Data
US 2013/0169951 A1    Jul. 4, 2013

(30) Foreign Application Priority Data

Sep. 17, 2010   (JP) .................................. 2010-209818

(51) Int. Cl.
*G01J 1/42*   (2006.01)
(52) U.S. Cl.
USPC ........................................................ 250/372
(58) Field of Classification Search
USPC ........................................................ 250/372
See application file for complete search history.

(56) References Cited

U.S. PATENT DOCUMENTS

| | | | |
|---|---|---|---|
| 5,500,533 A | 3/1996 | Ogawa et al. | |
| 5,824,320 A | 10/1998 | Rouillard et al. | |
| 8,049,179 B2 | 11/2011 | Miura et al. | |
| 2005/0036961 A1 | 2/2005 | Hansenne et al. | |
| 2012/0022472 A1 | 1/2012 | Miura et al. | |

FOREIGN PATENT DOCUMENTS

| | | | |
|---|---|---|---|
| EP | 2204646 A1 * | 7/2010 | ............ G01N 21/33 |
| JP | 07-167781 | 7/1995 | |
| JP | 09-506906 | 7/1997 | |
| JP | 2003-073250 | 3/2003 | |
| JP | 2005-060395 | 3/2005 | |
| JP | 2008-096151 | 4/2008 | |

(Continued)

OTHER PUBLICATIONS

International Search Report mailed on Sep. 13, 2011.

(Continued)

*Primary Examiner* — Kiho Kim
(74) *Attorney, Agent, or Firm* — IPUSA, PLLC

(57) ABSTRACT

An evaluation method for evaluating the ultraviolet protection effect of a measurement sample applied on a substrate includes measuring, at predetermined wavelength intervals, a change over time of a spectral transmission spectrum of the measurement sample within a predetermined wavelength range by irradiating light from a light source that includes ultraviolet light, visible light, and infrared light under a predetermined irradiation condition; establishing, based on the change over time of the spectral transmission spectrum, a correlation between a light irradiation time and an erythema effective dose per unit time, which is obtained by dividing an erythema effective dose of the measurement sample by an erythema effective dose per 1 MED; and calculating an in vitro rSPF predictive value for the measurement sample on the basis of a time until a cumulative erythema effective dose, which is obtained through time integration based on the correlation, reaches 1 MED.

6 Claims, 23 Drawing Sheets

(56) References Cited

FOREIGN PATENT DOCUMENTS

| JP | 4365452 | 11/2009 |
|----|---------|---------|
| JP | 4454695 | 4/2010 |
| WO | WO 2009/051222 | 4/2009 |
| WO | WO 2009/150883 | 12/2009 |

OTHER PUBLICATIONS

Sunscreen isn't enough, Journal of Photochemistry and Photobiology B: Biology 64 (2001) 105-108.

CIE Journal (1987) vol. 6, No. 1, 17-22.

Akira Ishikubo et al., "Shinki In Vitro Shigaisen Bogyosei Hyokaho no Kaihatsu", Journal of SCCJ, Mar. 20, 2003, vol. 37, No. 1, pp. 10 to 16.

Iveson R D, et.al., A study of the effect of anatomical site on sun protection factor efficiency using a novel UV delivery device, Journal of the Society of Cosmetic Chemists, 1995.10, vol. 46, No. 5, p. 271-280.

Reece B T, et.al., An in vitro method for screening sunscreen formulations for sun protection factor using a full-thickness skin model, Journal of the Society of Cosmetic Chemists, Dec. 1992, vol. 43, No. 6, p. 307-312.

Hiroshi Hayashi, Ryuzo Kobayashi, "Koshohin Kagaku no Tenbo o Saguru, Shigaisen Bogyo Seihin no Tenbo", Fragrance Journal, Jan. 15, 1996, vol. 24, No. 1, pp. 53 to 58.

\* cited by examiner

FIG.6

| Sample | Photostability | Emulsion type | in vivo SPF (mean ± SD) | UV filter |
|---|---|---|---|---|
| A | Photounstable | Oil in water (O/W) | 8.5 ± 1.2 | Ethylhexyl methoxycinnamate Butyl methoxydibenzoyl methane Phenylbenzimidazole sulfonic acid |
| B | Photostable | Water in oil (W/O) | 31.5 ± 3.7 | Titanium dioxide Zinc oxide |

FIG.17

| PANEL | APPLIED REGION | CALCULATED AVERAGE ROUGHNESS OF APPLIED REGION [Sa, μm] | ACTUAL AVERAGE APPLICATION DOSE * [mg/cm$^2$] | CALCULATED AVERAGE ROUGHNESS OF APPLICATION PLATE USED [Sa, μm] | SAMPLE | in vivo SPF (AVERAGE VALUE) | in vitro r SPF (AVERAGE VALUE) |
|---|---|---|---|---|---|---|---|
| A | CHEEK | 8.9 | 1.65 | 9.0 | X (O/W EMULSION) | 20.9 | 17.3 |
| A | ARM | 16.3 | 1.10 | 17.0 | X (O/W EMULSION) | 20.9 | 8.1 |
| A | BACK | 25.4 | 0.80 | 25.0 | X (O/W EMULSION) | 20.9 | 3.5 |
| B | CHEEK | 7.5 | 1.75 | 8.0 | Y (W/O EMULSION) | 33.8 | 21.9 |
| B | ARM | 12.1 | 1.35 | 12.0 | Y (W/O EMULSION) | 33.8 | 15.5 |
| B | BACK | 27.5 | 0.65 | 28.0 | Y (W/O EMULSION) | 33.8 | 4.2 |
| C | CHEEK | 11.2 | 1.65 | 11.0 | Z (W/O EMULSION) | 58.9 | 34.3 |
| C | ARM | 16.2 | 1.25 | 16.0 | Z (W/O EMULSION) | 58.9 | 21.7 |
| C | BACK | 23.4 | 0.55 | 23.0 | Z (W/O EMULSION) | 58.9 | 6.1 |

* AVERAGE FROM ACTUALLY APPLYING THE SAMPLE TO A 5×5 cm REGION ON FIVE OCCASIONS

ULTRAVIOLET PROTECTION EFFECT EVALUATION METHOD, EVALUATION APPARATUS, AND RECORDING MEDIUM

TECHNICAL FIELD

The present invention relates generally to a method of evaluating an ultraviolet protection effect, an evaluation apparatus, and a recording medium, and particularly to a technique for accurately evaluating the protective effect against ultraviolet light that is irradiated under real-life usage conditions and usage environments.

BACKGROUND ART

The SPF (Sun Protection Factor) is conventionally used as a measure for indicating the ultraviolet protection effect of cosmetic products that provide protection against sunburn from ultraviolet radiation (e.g., so-called sun care products). The SPF is obtained using an in vivo SFP determination method such as the world-recognized International SPF Test Method (CTFASA/COLIPA/JCIA/CTFA: May 2006) that involves evaluating erythema reactions of the human skin. The SPF is an indicator of the protection provided for the skin against sunburn from ultraviolet radiation, and is obtained by dividing the amount of ultraviolet radiation required to cause erythema when using a sun care product by the amount of ultraviolet radiation required to cause erythema without using the sun care product. For example, assuming ultraviolet light is irradiated under the same conditions, the degree of sunburn from exposure to ultraviolet radiation when using a sun care product with an SPF of 10 is equivalent to the degree of sunburn that may be sustained by the bare skin when being exposed to ten times the amount of ultraviolet radiation.

In determining the SPF, a solar simulator is used rather than sunlight, which may vary in intensity depending on the season or the environment. Also, the method of determining the SFP involves irradiating a fixed amount of ultraviolet light on the skin having the product applied and the skin without the product applied, and checking whether erythema has occurred the next day.

By using an SPF determined using the above method, the protective effect of a sun care product against ultraviolet radiation may be objectively evaluated. However, the above determination method requires the cooperation of a large number of human volunteers with various skin types as test subjects, and is also costly and time-consuming. Also, from an ethical standpoint, an in vitro determination method that does not involve testing on human subjects may be favored for evaluating the ultraviolet protection effect of a product still in the development stage, for example. Thus, in recent years and continuing, techniques are being developed for calculating in vitro SPF predictive values having high correlation with in vivo SPF values by basically re-creating the in vivo SPF determination method (See, e.g., Japanese Patent No. 4365452, and Japanese Patent No. 4454695).

It is noted that various accommodations are made with regard to measurement conditions to reduce the burden on human test subjects in the in vivo SPF determination methods currently being used.

For example, according to one technique, to reduce the measurement time, light at an intensity several tens of times stronger than the intensity of actual sunlight is irradiated on the skin so that an erythema reaction would occur sooner. According to another technique, to facilitate visual evaluation of only an erythema reaction from ultraviolet radiation, visible light and infrared light are cut out from the irradiation spectrum of a solar simulator so that redness of the skin due to the effects of heat may be prevented from occurring. However, these measurement conditions are different from irradiation conditions of actual sunlight under which the sun care product is used in real-life.

Also, in the in vivo SPF determination method, the amount of a sample applied to the skin (application dose) is uniformly fixed at 2.00 mg/cm$^2$. However, in real-life, there are variations in the amount and manner in which a user applies a sun care product. There are publications that suggest that on average, users apply sunscreen at approximately 0.5-1.5 mg/cm$^2$ (See, e.g., Sunscreen isn't enough, Journal of Photochemistry and Photobiology B: Biology 64 (2001) 105-108).

Although SPF values obtained using conventional in vivo SPF determination methods enable "relative" comparison of the ultraviolet protection effects of different products, they do not provide predictions based on a quantitative "absolute" measure of the "ultraviolet protection effect under actual usage environments and usage conditions" for each individual user.

Thus, even when a consumer uses a product with an SPF value suitable for a particular scene, the user may still sustain sunburns. It has been believed that this is primarily due to discrepancies in the usage conditions of the consumer such as the application dose by the consumer being less than the application dose used in the in vivo SPF determination method or unevenness of application.

It is important from a consumer protection standpoint to provide information predicting the ultraviolet protection effect of a product under actual usage environments and usage conditions. However, an in vitro SPF evaluation method for predicting the ultraviolet protection effect based on usage environments and usage conditions in real-life (referred to as "real-life SPF" or "rSPF" hereinafter) has yet to be developed.

One reason for the absence of such in vitro SPF evaluation method may be due to the fact that SPF values obtained using the conventional in vivo SPF determination methods have been perceived as "absolute" measures of the ultraviolet protection effect.

However, with the disclosure of information on the impact of consumer usage conditions such as the actual application dose on in vivo SPF values as exemplified by the above publication, there is a growing recognition of the impact of usage conditions on the "absolute" measure of the ultraviolet protection effect.

On the other hand, the impact of the usage environment such as the shape and intensity of sunlight on the "absolute" measure of ultraviolet protection effect has not been taken under consideration.

Further, a second reason for the absence of the in vitro SPF evaluation method for predicting the real-life SPF may be due to the unavailability of a highly sensitive ultraviolet radiation detection/evaluation apparatus for evaluating the real-life SFP through in vitro testing or an evaluation program having an algorithm for accumulating the amount of ultraviolet radiation to which the skin may be exposed over time and analyzing the evaluation results based on the detected ultraviolet radiation.

Also, it is noted that evaluating the real-life SPF through in vivo testing using human test subjects is not realistically possible in consideration of the burden imposed on the human test subjects from the long hours of restraint and the difficulty of distinguishing between redness of the skin caused by infrared light contained in sunlight and erythema caused by ultraviolet radiation.

As can be appreciated from above, in vitro testing that does not cause a burden on human test subjects and does not require distinguishing erythema caused by ultraviolet radiation from redness of the skin caused by heat may be suitable for predicting the real-life SPF.

It is noted that conventional in vitro SPF evaluation methods are designed to basically re-creating an in vivo SPF method such as the world-recognized International SPF Test Method (CTFASA/COLIPA/JCIA/CTFA: May 2006). That is, these in vitro SPF evaluation methods are focused on achieving high intra-laboratory reproducibility and inter-laboratory reproducibility, and accurately predicting the in vivo SPF values that may be obtained in the event the in vivo SPF evaluation method were used. Thus, the reliability of such in vitro SPF evaluation methods is assessed based on the degree of correlation with corresponding in vivo SPF values.

In other words, these conventional in vitro SPF evaluation methods and in vivo SPF evaluation methods do not reflect the protective effect against ultraviolet radiation based on the usage environments and usage conditions of actual users. Thus, SPF values obtained from conventional evaluation methods may be inadequate as information accompanying a product from a consumer protection standpoint. For example, a user may sustain sunburns by using a sun care product under conditions or environments that are different from the conditions and environment under which the SFP value of the product was obtained from a conventional in vitro SPF evaluation method or in vivo SPF evaluation method.

Thus, a technique is desired for quantitatively predicting an "ultraviolet protection effect under actual usage environments and usage conditions" for each individual through in vitro testing.

It is an object of at least one embodiment of the present invention to provide an ultraviolet protection effect evaluation method, evaluation apparatus, and a recording medium for accurately evaluating the ultraviolet protection effect of a sample under real-life usage conditions and usage environments.

SUMMARY OF THE INVENTION

Means for Solving the Problem

According to one embodiment of the present invention, an evaluation method for evaluating the ultraviolet protection effect of a measurement sample applied on a substrate is provided that involves a first step of measuring, at predetermined wavelength intervals, a change over time of a spectral transmission spectrum of the measurement sample within a predetermined wavelength range by irradiating light from a light source that includes ultraviolet light, visible light, and infrared light under a predetermined irradiation condition; a second step of establishing, based on the change over time of the spectral transmission spectrum, a correlation between a light irradiation time and an erythema effective dose per unit time, which is obtained by dividing an erythema effective dose of the measurement sample by an erythema effective dose per 1 MED; and a third step of calculating an in vitro rSPF predictive value for the measurement sample on the basis of a time until a cumulative erythema effective dose, which is obtained through time integration based on the correlation, reaches 1 MED.

According to another embodiment of the present invention, an evaluation apparatus for evaluating an ultraviolet protection effect of a measurement sample applied on a substrate is provided that includes a temporal change measurement unit for measuring, at predetermined wavelength intervals, a change over time of a spectral transmission spectrum of the measurement sample within a predetermined wavelength range by irradiating light from a light source that includes ultraviolet light, visible light, and infrared light under a predetermined irradiation condition; a correlation setting unit for establishing, based on the change over time of the spectral transmission spectrum, a correlation between an irradiation time and an erythema effective dose per unit time, which is obtained by dividing an erythema effective dose of the measurement sample by an erythema effective dose per 1 MED; and a SPF predictive value calculation unit for calculating an in vitro rSPF predictive value for the measurement sample on the basis of a time until a cumulative erythema effective dose, which is obtained through time integration based on the correlation, reaches 1 MED.

According to an aspect of the present invention, an ultraviolet protection effect of a sample in real-life ultraviolet radiation conditions under real-life usage conditions may be accurately evaluated.

BRIEF DESCRIPTION OF THE DRAWINGS

FIG. 6 is a table illustrating exemplary samples;

FIG. 17 is a table illustrating exemplary calculation results of in vitro rSPF values obtained from applying three different types of sample bases on three different regions.

EMBODIMENTS FOR IMPLEMENTING THE INVENTION

According to an embodiment of the present invention, a numeric value representing an ultraviolet protection effect under actual sunlight is predicted by arranging a "light irradiation spectrum" to simulate an actual sunlight spectrum and setting a "light irradiation intensity" to be close to the intensity of actual sunlight. In an evaluation according to the present embodiment, a plate (substrate) having an average roughness close to that of the skin (e.g., Sa value=approximately 17 μm) and a simplified surface profile based on the configuration of a skin replica is used as a "skin substitute film" and a sample is applied on the plate using an "actual sample application dose" and an "actual manner of application by a user."

In the present embodiment, at least one of a "light source spectrum," a "light source intensity," an "application dose," or a "calculated average roughness (Sa value) of the application plate" is set equal to a value corresponding to a real-life condition. For example, the light source spectrum may be arranged to irradiate light having a light source spectral waveform including ultraviolet light as well as visible light and infrared light to simulate natural sunlight. Also, the light source intensity may be arranged to be close to the intensity of actual sunlight. However, as is described in detail below, the real-life SPF predictive value is not affected by the light source intensity when the light source intensity is within a certain range. Thus, in a preferred embodiment, the light source intensity is arranged to be approximately 0.001-20.0 MED/min. Further, the calculated average roughness (Sa value) of the application plate is preferably arranged to be approximately 0.01-400 μm.

In the following, certain preferred embodiments of an evaluation method of an ultraviolet protection effect, an evaluation apparatus, and a recording medium of the present invention are described with reference to the accompanying drawings.

<Evaluation Apparatus: Exemplary Apparatus Configuration>

Figure 1:
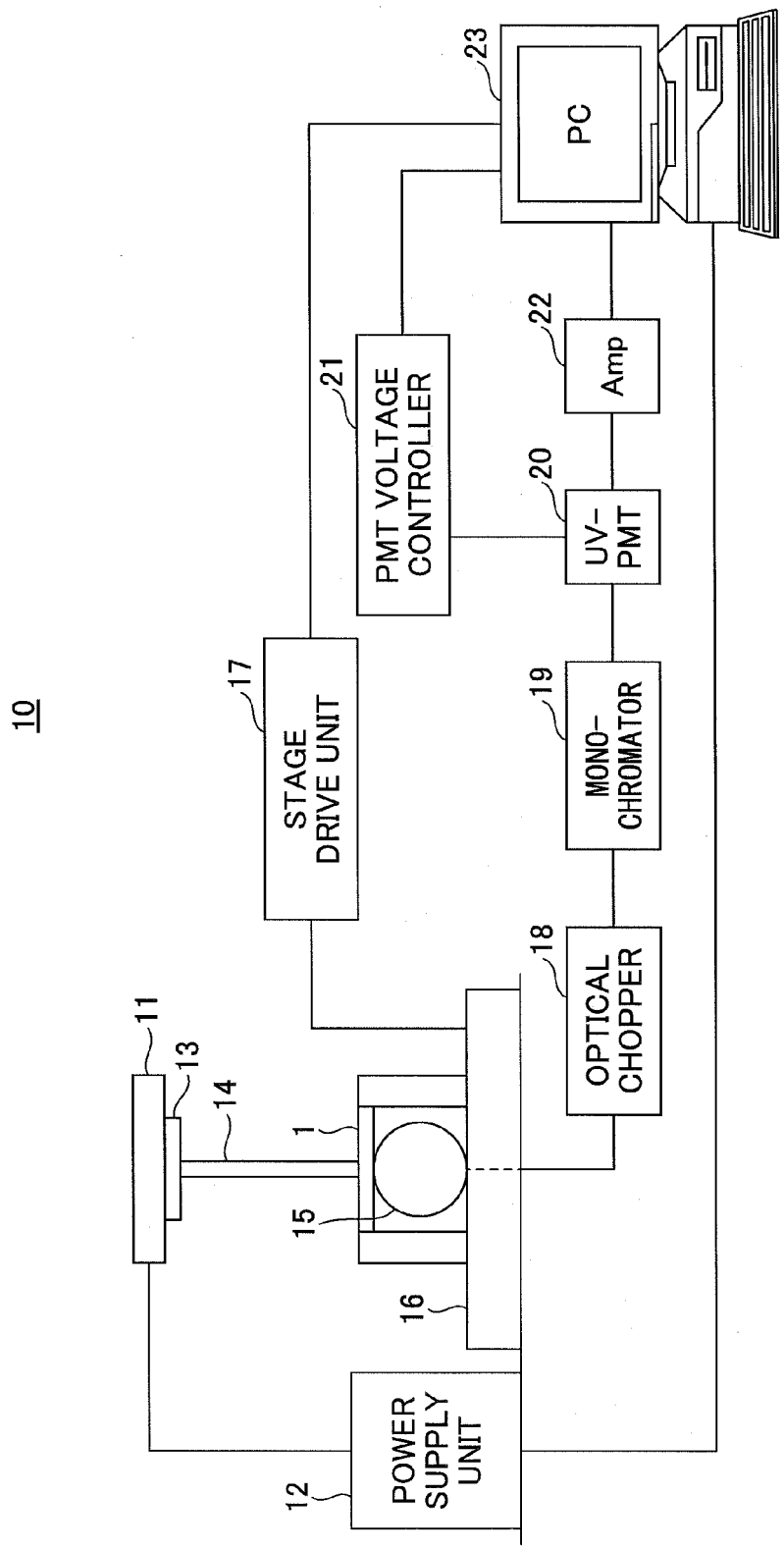
FIG. 1 is a diagram illustrating an exemplary overall configuration of an evaluation apparatus for evaluating an ultraviolet protection effect according to an embodiment of the present invention.

FIG. 1 is a diagram showing an exemplary configuration of an evaluation apparatus for evaluating an ultraviolet protection effect according to an embodiment of the present invention. The evaluation apparatus 10 shown in FIG. 1 is an apparatus for measuring a sample 1 (reference sample or measurement sample (test sample)) and includes a light source 11, a power source supply unit 12, a filter 13, an optical fiber 14, an integrating sphere 15, a stage 16, a stage drive unit 17, an optical chopper 18, a monochromator 19 corresponding to a spectrometer, a UV-PMT (Photo Multiplier Tube) 20 corresponding to a light detector, a PMT voltage controller 21, a signal amplifier (Amp) 22, and a PC (Personal Computer) 23 corresponding to a main control unit.

The light source 11 may be a xenon lamp corresponding to a white light source including ultraviolet light, visible light, and infrared light, for example. However, the present invention is not limited to such an example. Also, it is noted that the xenon lamp corresponding to the white light source may be used as a solar simulator.

That is, the light source spectrum used in the present embodiment may include an ultraviolet light range, a visible light range, and an infrared light range. For example, a light source having a wavelength of approximately 200-1000 nm may be used.

The power supply unit 12 supplies power to the light source 11 at a predetermined timing and at a predetermined intensity to adjust the light source intensity of the light source 11. For example, the power supply unit 12 may adjust the light intensity of a solar simulator using a commercial radiometer (e.g., Model No. 3D-600 or PMA-2100 by Solar Light Company, Inc.).

The filter 13 is arranged near the light source 11 along the travelling direction of the light from the light source 11 and is configured to correct the ultraviolet light spectrum of the light generated from the light source 11. It is noted that the filter 13 filters the light irradiation spectrum of the light irradiated from the light source 11 to simulate an actual sunlight spectral waveform using one or more optical filters such as a short wavelength cut filter, a long wavelength cut filter, a band pass filter, an ND filter, for example.

The resulting spectrum (simulated natural sunlight) is close to that of natural sunlight and is quite different from the spectrum of an artificial solar simulator that is used in an in vivo SPF determination method. It is noted that the spectrums of the simulated natural sunlight and the artificial solar simulator are described in detail below.

Also, the filter 13 may be switched according to the type of the light source 11 or the type of the sample 1 used, for example. In one preferred embodiment, a sliding mechanism that moves left-to-right or rotates around in a circle, for example, may be arranged so that the filter 13 may be automatically switched.

The optical fiber 14 is arranged near the filter along the traveling direction of the light from the filter 13 and is configured to guide light beams passing through the filter 13 towards the sample 1 and the integrating sphere 15.

The integrating sphere 15 receives light beams passing through the sample 1, focuses the light beams, and spatially integrates the light beams to have them uniformly distributed. That is, the integrating sphere 15 introduces light that has passed through the sample 1 inside the sphere, and by multiple scattering reflections, obtains a uniform intensity distribution of the light. It is noted that the uniform intensity distribution is proportional to the distribution of the light source intensity. It is noted that in some embodiments, the integrating sphere 15 may be omitted.

The stage 16 is driven and controlled by the stage drive unit 17 to move the integrating sphere 15 in horizontal (left-right) or vertical (up-down) directions at a predetermined timing. Further, the stage 16 may move the integrating sphere 15 diagonally at a predetermined angle. In this way, the position of the sample 1 through which light beams from the optical fiber 14 passes may be moved, and light beams that pass through the sample 1 at a predetermined position may be incident on the integrating sphere 15.

It is noted that the stage 16 may include a sample stage on which the sample 1 may be placed. In one preferred embodiment, the sample stage may be configured to hold and fasten the outer periphery or a portion of the sample 1. In this way, the location at which light is to be irradiated on the sample 1 may be arbitrarily moved.

The stage drive unit 17 moves the stage 16 to a predetermined position at a predetermined timing based on a control signal from the PC 23.

The optical chopper 18 converts a continuous spectrum of light including ultraviolet light, visible light, and infrared light from the integrating sphere 15 into a pulsed light at a given frequency. For example, the optical chopper 18 may be able to operate at a frequency range from 5 Hz to 20,000 Hz, for example, and its chopping frequency may be adjusted according to various factors such as the capability of the integrating sphere 15, the filter 13, and the light source 11, for example.

The monochromator 19 spatially disperses light of a wide wavelength range and extracts only a narrow wavelength range from the dispersed light using a slit, for example. The monochromator 19 may be capable of dispersing, at predetermined wavelength intervals, light from the optical chopper 18 including not only ultraviolet light but also visible light and infrared light within a wavelength range of approximately 200-1000 nm.

It is noted that the predetermined wavelength intervals at which light is dispersed may be at 0.5 nm intervals, at 1 nm intervals, or at 5 nm intervals, for example, but is not limited to such wavelength intervals. However, in the example described below, it is assumed that measurements are made at 1 nm intervals. The light dispersed by the monochromator 19 is output to the UV-PMT 20.

It is noted that in a preferred embodiment, a double monochromator is used as the monochromator 19 in order to reduce stray light, for example. However, the present invention is not limited to such embodiment, and a single monochromator or a triple monochromator may be used as the monochromator 19, for example.

It is noted that the monochromator 19 corresponding to a spectrometer may be arranged to have a spectroscopic sensitivity characteristic to ultraviolet light, for example, and may use a diffraction grating having high sensitivity to the ultraviolet light range of 200-400 nm to realize sensitive spectroscopy, for example. In one specific example, a concave surface diffraction grating by Shimadzu Corporation (Model No. 10-015) may be used. However, the present invention is not limited to such an example.

The UV-PMT 20 corresponding to a light detector uses an optical sensor to detect light beams of the ultraviolet range (UV range) that is dispersed by the monochromator 19 corresponding to a spectrometer, and converts the intensities of the light beams with various wavelengths into electric current signals or voltage signals. It is noted that the generation of these signals is controlled by the PMT voltage controller 21. That is, the UV-PMT 20 of the present embodiment is a highly sensitive light detector that is capable of adding a current amplification function when converting light energy into electric energy using the photoelectric effect.

The PMT voltage controller 21 performs predetermined voltage control of the UV-PMT 20 so that the UV-PMT 20 may convert a wavelength intensity into a corresponding electric current signal or voltage signal.

Also, the signal output from the UV-PMT 20 is amplified by the signal amplification unit (Amp) 22 and output to the PC 23. It is noted that the UV-PMT 20 is not limited to a photomultiplier tube. For example, a semiconductor light detector made of In, Ga, N, Al, and O may be used as the UV-PMT 20.

The PC 23 is a main control unit that controls the overall operations of the various units of the evaluation apparatus 10. For example, the PC 23 generates control signals and outputs the control signals to relevant components such as the power supply unit 12, the stage drive unit 17, and the PMT controller 21 so that relevant operations may be performed under predetermined conditions at predetermined timings.

For example, the PC 23 may control on/off operations of the light source 11. Also, the PC 23 may control the intensity of light dispersed at predetermined wavelength intervals (e.g., 1 nm) from the UV-PMT 20 and calculate the final in vitro rSPF predictive value for the measurement sample. Also, the PC 23 may receive data from the UV-PMT 20, process the data so that it may be easily understood by a user, generate a screen that displays the resulting data, output the resulting data on recording paper, or save the resulting data on a recording medium, for example. Also, the PC 23 may evaluate the ultraviolet protection effect of a sample in real-life ultraviolet light irradiation environments under real-life usage conditions based on the acquired data.

It is noted that a general-purpose personal computer may be used as the PC 23, for example, and the various functions of the evaluation apparatus 10 may be executed when a user command is input via an input unit, for example.

<Evaluation Apparatus: Exemplary Functional Configuration>

Figure 2:
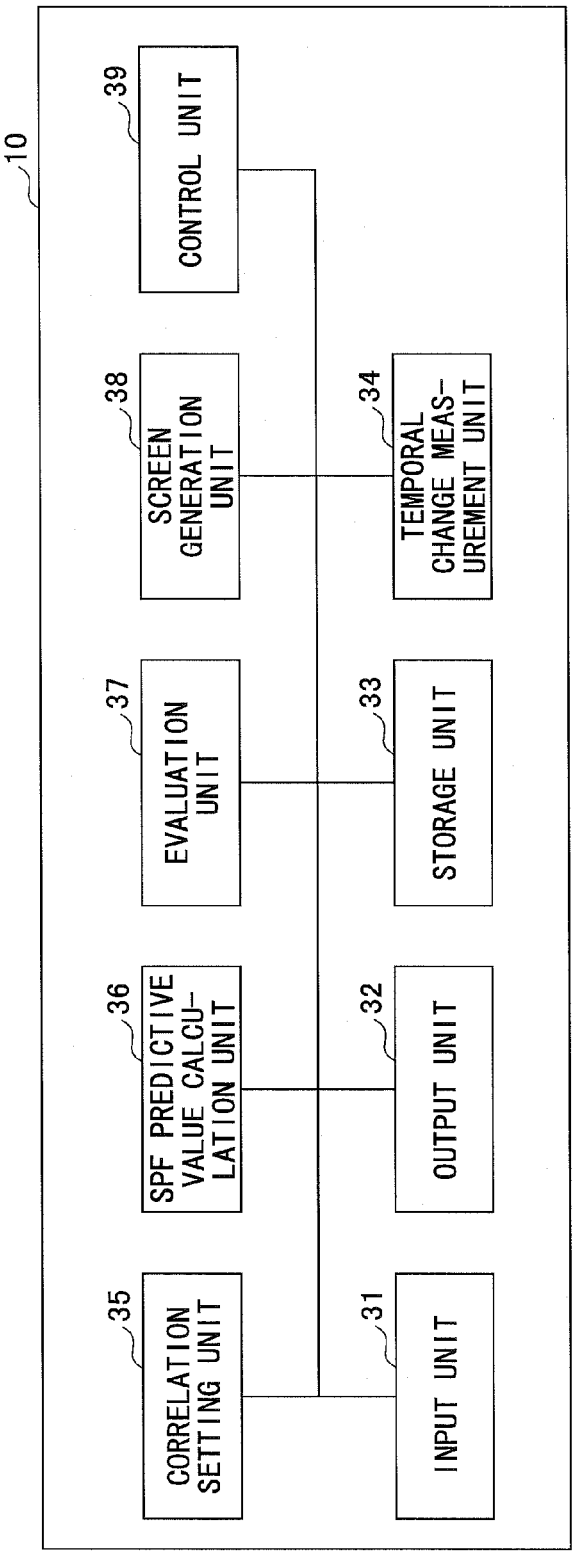
FIG. 2 is a diagram illustrating an exemplary functional configuration of the evaluation apparatus for evaluating an ultraviolet protection effect.

In the following, a functional configuration of the evaluation apparatus 10 is described. FIG. 2 is a diagram showing an exemplary functional configuration of the evaluation apparatus 10 for evaluating an ultraviolet protection effect according to the present embodiment.

The evaluation apparatus 10 shown in FIG. 2 includes an input unit 31, an output unit 32, a storage unit 33, a temporal change determination unit 34, a correlation setting unit 35, an SPF predictive value calculation unit 36, an evaluation unit 37, a screen generation unit 38, and a control unit 39.

The input unit 31 may be arranged at the PC 23, for example, and is configured to accept an evaluation start command from a user or various data inputs for prompting the output unit 32 to output measurement results, for example. It is noted that the input unit 31 may be a keyboard or a pointing device such as a mouse, for example.

The output unit 32 may be arranged at the PC 23, for example, and is configured to display/output data input via the input unit 31 or data on the execution of processes based on the input data, for example. It is noted that the output unit 32 may be display unit or a speaker, for example. The output unit 32 may also have a printing function for outputting various data. In this way, simplified measurement results, calculation results, and/or evaluation results may be printed on a printing medium such as paper and provided to a user, for example.

The storage unit 33 may be arranged at the PC 23, for example, and is configured to store various types of data such as measurement results obtained by the temporal change measurement unit 34, the settings made by the correlation setting unit 35, calculation results obtained by the SPF predictive value calculation unit 36, evaluation results obtained by the evaluation unit 37, and screens generated by the screen generation unit 38. Also, the storage unit 33 may retrieve the various types of stored data and/or various types of setting information (parameters) that are set up beforehand for executing various functions as is necessary.

The temporal change measurement unit 34 measures a change over time of the spectral transmission spectrum of the sample 1 (reference sample or measurement sample (test sample)) within a predetermined wavelength range by irradiating light from a light source that includes ultraviolet light, visible light, and infrared light (e.g., wavelength of approximately 200-1000 nm) under a predetermined light irradiation condition. For example, the temporal change measurement unit 34 may use the light detector 20 to measure, at predetermined wavelength intervals (e.g., 1 nm), a change over time of the spectral transmission spectrum of the measurement sample 1 (reference sample or measurement sample (test sample)) by irradiating light from a light source that includes ultraviolet light within a wavelength range of 290-400 nm. Also, the temporal change measurement unit 34 measures a change over time of the spectral transmission spectrum of the sample 1 by irradiating light for a predetermined light irradiation time.

It is noted that because the temporal change measurement unit 34 can measure a change over time of the spectral transmission spectrum at arbitrary time intervals, conditions such as processing time may be easily adjusted, for example. Thus, conditions such as the evaluation processing time may be reduced as is necessary. Also, the temporal change measurement unit 34 measures a change over time of the spectral transmission spectrum of the sample 1 caused by photodegradation. Thus, in vitro rSPF predictive values reflecting photodegradation of a sample caused by light irradiation may be obtained.

The correlation setting unit 35 establishes the correlation between the light irradiation time and the erythemal effective dose per unit time based on the change over time of the spectral transmission spectrum of the sample 1 obtained by the temporal change measurement unit 34 corresponding to a function of the PC 23.

That is, the correlation setting unit 35 determines, based on the temporal change measurements of the temporal change measurement unit 34, the correlation between the change over time of the spectral transmission spectrum and the erythema effective dose (temporal erythema effective dose). Specifically, based on the temporal change measurements obtained by the temporal change measurement unit 34, the correlation setting unit 35 determines the correlation between the light irradiation time and the erythemal effective dose per time unit, which is obtained by dividing the erythemal effective dose of the sample 1 by the erythemal effective dose per 1 MED (Minimal Erythema Dose).

The erythema effective dose used in the correlation setting unit 35 may be calculated by multiplying the transmitted light intensity of each wavelength by a predetermined erythema factor (likelihood of reddening). In this way, the erythema effective dose may be accurately calculated. For example, the erythema factors disclosed in CIE Journal (1987) 6:1, 17-22 may be used to calculate the erythema effective dose. However, the present invention is not limited to such an example, and erythema factors disclosed in other publications may be used as well. Also, it is noted that the above-described manner of determining the correlation between the light irradiation time and the erythema effective dose per time unit is disclosed in Japanese Patent No. 4365452, for example. However, the present invention is not limited to the above manner of determination.

The SPF predictive value calculation unit 36, as a function of the PC 23, calculates an in vitro rSPF predictive value for the sample 1 on the basis of the time it takes for a cumulative erythema effective dose, which is obtained by time integration of the erythema effective dose based on the correlation determined by the correlation setting unit 35, to reach 1 MED. It is noted that 1 MED refers to the threshold amount of ultraviolet light required to cause minimal erythema at a tested region of a test subject in conducting in vivo SPF measurements.

The SPF predictive value calculation unit 36 may also correct an in vitro rSPF predictive value of a sample using at least one of an in vitro rSPF predictive value obtained for a predetermined reference sample, the light source intensity used to evaluate to reference sample, or the sample application dose at which the reference sample was applied to a skin substitute film.

Specifically, first, the above-described measurement and determination processes are performed by the temporal change measurement unit 34 and the correlation setting unit 35 on the predetermined reference sample, and the SPF predictive value calculation unit 36 calculates an in vitro rSPF predictive value for the reference sample on the basis of the time it takes for the cumulative erythema effective dose, which is obtained by time integration of the erythema effective dose based on the correlation determined by the correlation setting unit 35, to reach 1 MED. The calculated in vitro rSPF predictive value of the reference sample may be stored in the storage unit 33 along with other relevant data such as the light source intensity used, and the application dose of the reference sample applied to the skin substitute film, for example.

Then, the SPF predictive value calculation unit 36 calculates an in vitro rSPF predictive value for a measurement sample in the manner described above, and corrects the calculated in vitro rSPF predictive value of the measurement sample based on at least one of the in vitro rSPF predictive value for the reference sample, the light source intensity, or the sample application dose.

In this way, an in vitro rSPF predictive value that accurately reflects an in vivo rSPF value may be calculated. It is noted that that data associated with the reference sample such as the in vitro rSPF predictive value, the light source intensity, and/or the sample application dose may also be used to correct an in vivo rSPF value obtained for another reference sample, for example.

The evaluation unit 37 makes an evaluation of the protective effect against ultraviolet light irradiated under real-life usage conditions and usage environments based on the measurement results obtained by the temporal change measurement unit 34 and the calculations results obtained by the SPF predictive value calculation unit 36, for example.

The screen generation unit 38 generates a screen that displays the processing results obtained by the above-described units and enables setting of various conditions, for example. The screen generation unit 38 also prompts the output unit 32 to output the generated screen. It is noted that exemplary screens that may be generated by the screen generation unit 38 are described below.

The control unit 39, as a function of the PC 23, controls the overall operations of the various units of the evaluation apparatus 10. For example, based on a command input by a user via the input unit 31, the control unit 39 may control the above-described operations such as the measurement of the change over time of the spectral transmission spectrum, the determination of the correlation, and the calculation and correction of the in vitro rSPF predictive value. Also, the control unit 39 may control the on/off operations of the light source 11 by the PC 23, for example.

<Evaluation Apparatus 10: Hardware Configuration>

It is noted that an evaluation process according to an embodiment of the present invention may be performed by the above-described evaluation apparatus 10 by generating an execution program (evaluation program) that enables a computer to execute the various functions of the evaluation apparatus 10, and installing the program in the PC 23, which may be a general-purpose personal computer or server, for example.

Figure 3:
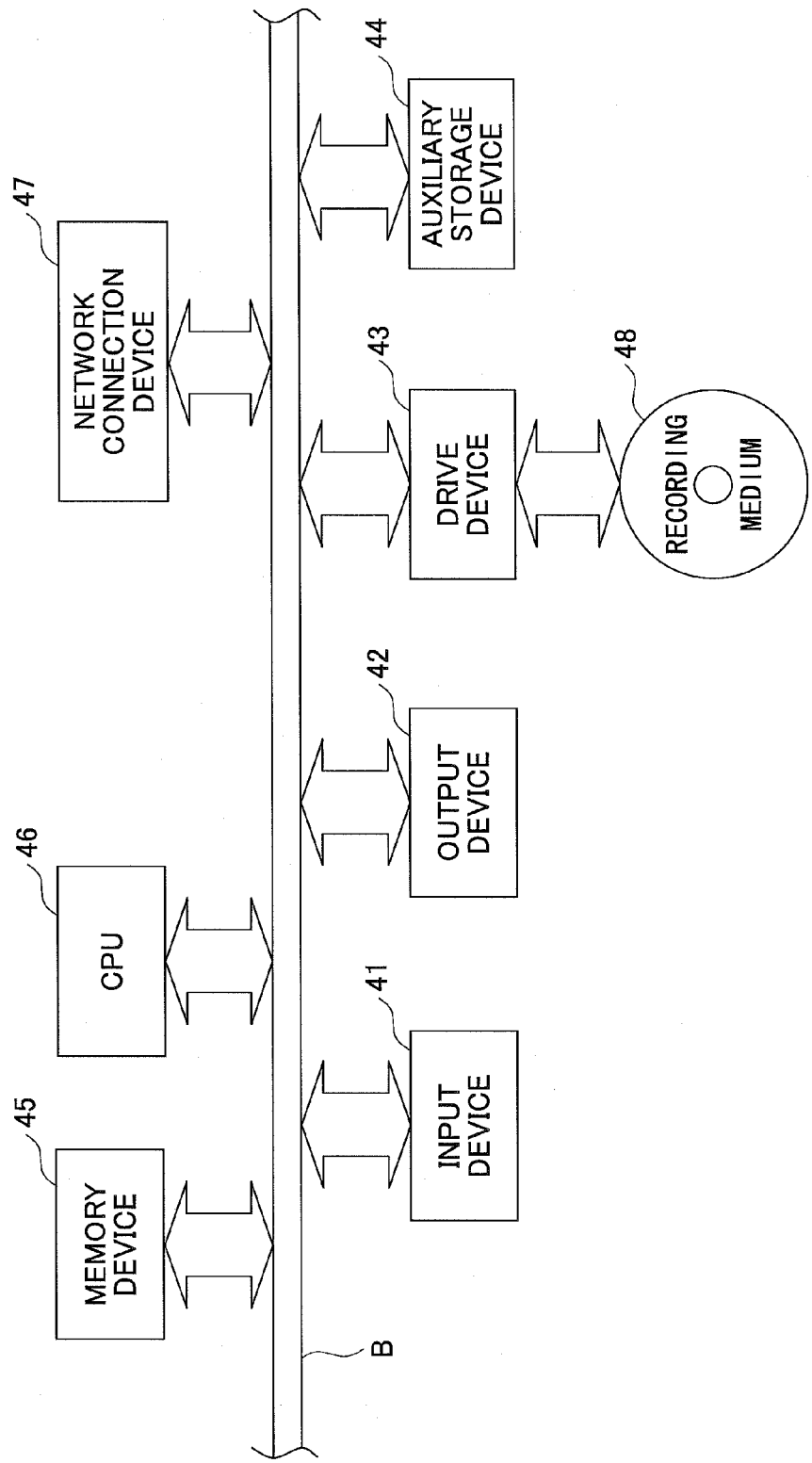
FIG. 3 is a diagram illustrating an exemplary hardware configuration of a computer that is capable of executing an evaluation process according to an embodiment of the present invention.

In the following, an exemplary hardware configuration of a computer that may execute an evaluation process according to an embodiment of the present invention is described. FIG. 3 is a diagram illustrating such an exemplary hardware configuration of the computer for executing the evaluation process according to the present embodiment.

The computer shown in FIG. 3 includes an input device 41, an output device 42, a drive device 43, an auxiliary storage device 44, a memory device 45, a CPU (Central Processing Unit) 46 that performs overall control operations, and a network connection device 47. These component devices are interconnected by a bus B.

The input device 41 includes a keyboard and a pointing device such as a mouse that may be operated by a user. The input device 41 inputs various operational signals from the user such as a command to execute a program. The output device 42 includes a display device for displaying various windows and data for operating the computer. The output device 41 may display various items of information such as the progress or result of executing a program based on a control program of the CPU 46.

In the present embodiment, the execution program to be installed in the computer is provided by a recording medium 48, which may be a portable medium such as a USB (Universal Serial Bus) memory or a CD-ROM. The recording medium 48 storing the execution program may be loaded in the drive device 43, and the execution program stored in the recording medium 48 may be installed in the auxiliary storage device 44 via the drive device 43.

The auxiliary storage device 44 may be a hard disk, for example, and is configured to store programs such as the execution program of the present embodiment and control programs of the computer and input/output the stored programs as is necessary.

The memory device 45 stores an execution program that is read from the auxiliary storage device 44 by the CPU 46. The memory device 45 may be a ROM (Read Only Memory) or a RAM (Random Access Memory), for example.

The CPU 46 controls overall operations of the computer such as various computational operations and data input/output operations of hardware components based on control programs such as the OS (Operating System) of the computer and execution programs stored in the memory device 45. In this way, the CPU 46 enables the execution of various processes for the evaluation of the ultraviolet protection effect according to the present embodiment. Also, during execution of a program, the CPU 46 may obtain various items of information from the auxiliary storage device 44 and store program execution results.

The network connection device 47 may establish connection with a communications network to obtain an execution program from another termination connected to the communications network or provide the execution program of the present embodiment or the results of executing the execution program to the other terminal, for example.

The evaluation process for evaluating the ultraviolet protection effect according to the present embodiment may be executed by a computer having the above-described hardware configuration. Also, the evaluation process according to the present embodiment may be easily executed by a general-purpose computer by installing the execution program according to the present embodiment.

<Ultraviolet Protection Effect Evaluation Process Steps>

Figure 4:
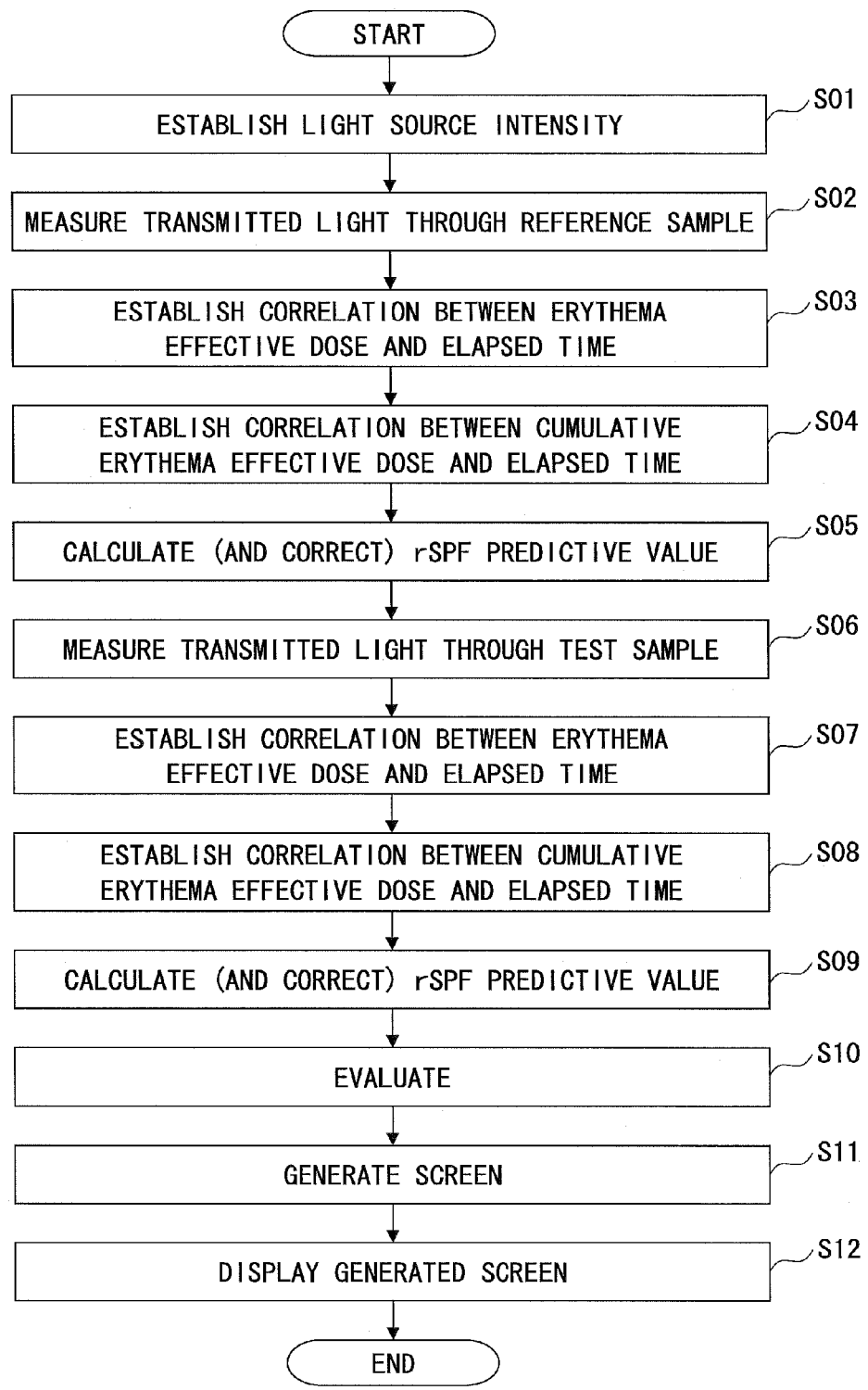
FIG. 4 is a flowchart illustrating exemplary process steps of the evaluation process for evaluating an ultraviolet protection effect.

In the following, process steps of the evaluation process for evaluating the ultraviolet protection effect according to the present embodiment are described. FIG. 4 is a flowchart illustrating exemplary process steps of the evaluation process for evaluating the ultraviolet protection effect according to the present embodiment.

In the evaluation process illustrated in FIG. 4, first, the light source intensity is established (S01). Specifically, the light intensity of a solar simulator may be adjusted using a commercial radiometer (e.g., Model No. 3D-600 or PMA-2100 by Solar Light Company, Inc.), for example. It is noted that when the light source intensity is within a certain range, it does not affect the rSPF predictive value, as is described in detail below. Thus, the light source is preferably adjusted to be within a range of approximately 0.5-15 MED/min, and more preferably within a range of approximately 1-5 MED/min, in accordance with a corresponding in vivo SPF measurement method, for example.

Next, the transmitted light through the reference sample is measured (S02). For example, this may be performed by preparing a blank skin substitute film, a skin substitute film coated with a non-UV absorbing substance such as glycerin, and a skin substitute film coated with a given reference sample; and measuring the transmitted light through these skin substitute films. It is noted that a commercially available PMMA (Polymethyl Methacrylate) plate (e.g., 50×50 mm) may be used as the skin substitute film, for example. However, the present invention is not limited to such an example. Further, the surface of the PMMA plate is preferably arranged to have a calculated average surface roughness (Sa value) of approximately 0.01-400 μm by processing the surface through sand blasting or molding the plate into a configuration simulating the skin surface, for example.

On this plate, a reference sample (e.g., glycerin) is applied at an application dose of $0.75/cm^2$, for example. Then, the reference sample is spread evenly on the surface of the PMMA plate using the finger tips or covered fingertips for approximately one minute, for example. It is noted that Japanese Patent Application No. 2009-081400, which was filed by the present inventors, discloses an exemplary manner of applying the sample. However, the present invention is not limited to such disclosed method of application.

It is noted that in other embodiments, the sample may be applied on the skin substitute film using an applicator device rather than using the fingertips, for example. Also, it is noted that the application dose at which a sample is applied to the skin substitute film is not limited to a particular application dose.

The reference sample to be applied is used not only as the skin substitute film but also as a blank of the measurement sample. Therefore, a liquid substance having a transmittance of at least 50% within a wavelength range of at least 290-400 nm is preferably applied on the skin substitute film.

Also, in a preferred embodiment, after applying the sample, a predetermined drying time (e.g., about 15 minutes) is provided before starting measurement.

The ultraviolet protection effect of the sample on the skin substitute film may be predicted using a so-called blank measurement, in which case a liquid material such as glycerin may be used. However, samples of SPF4 and SPF15 may be used instead as a standard sample (a standard sample with a predetermined SPF) in conformity with a corresponding in vivo SPF measurement method, for example. In other words, samples having a known and arbitrary SPF may be used as the reference sample. In this way, accuracy of the evaluation may be improved.

It is noted that in certain embodiments, a liquid substance such as glycerin is used as the reference sample to provide a so-called blank measurement for predicting the ultraviolet protection effect on the skin substrate film. However, in other embodiments, in accordance with an in vivo measurement method, a sample with SPF 4 or SPF 15 may be used as a standard sample (i.e., standard sample with a fixed value from which the same value would always be obtained when tested). In other words, when measuring the transmitted light at a predetermined wavelength range, a given sample with a known in vivo SPF value may be used as the reference sample. In this way, the accuracy of the evaluation may be improved, for example.

It is noted that specific examples of measuring the transmitted light through the reference sample in step S02 are described later.

Next, based on the results of the measurement of transmitted light obtained in step S02, the correlation between the erythema effective dose and the elapsed time is established by converting each spectral transmission spectrum of a temporal change (a temporal change in the spectrum) into an erythema effective dose for a corresponding time (S03). Specifically, a correlation such as correlation equations may be established based on the relationship between the erythema effective doses obtained from plural temporal changes in the spectrum and the elapsed time, for example.

Next, based on the correlation such as correlation equations established in step S03, the erythema effective doses at predetermined times are calculated, and the correlation between the cumulative erythema effective dose and the elapsed time is established based on the calculation results (S04). It is noted that a detailed description of establishing the correlation between the cumulative erythema effective dose and the elapsed times is given below.

Also, based on the correlation between the cumulative erythema effective dose and the elapsed time obtained in step S04, an rSPF predictive value of the reference sample is calculated (S05). Also, in step S05, the calculated rSPF predictive value may be corrected based on at least one of a previously obtained in vitro rSPF predictive value, light source intensity, or application dose at which a sample is applied on the skin substitute film. It is noted that settings disclosed in Japanese Patent No. 4365452 may be used in step S05, for example. However, the present invention is not limited to this example.

Next, a test sample (measurement sample) is applied on the skin substitute film, and the transmitted light through this test sample is measured (S06). It is noted that the test sample may be applied to the skin substitute film in a manner similar to the above manner of applying the reference sample.

As with the reference sample, the test sample may be applied at a rate of 0.75 mg/cm$^2$, for example. Thereafter, the test sample may be spread evenly on the surface of the PMMA plate using the fingertips or covered fingertips for about one minute, for example. In another example, an applicator device for applying the test sample on the skin substitute film may be used instead of the fingertips. Also, in a preferred embodiment, a predetermined drying time (e.g., about 15 minutes) is provided before starting measurement. It is noted that specific examples of measuring the transmitted light through the test sample in step S06 are described below. Also, it is noted that the application dose at which the test sample is applied to the skin substitute film is not limited to 0.75 mg/cm$^2$. The application dose may be increased or increased as desired according to real-life usage conditions as long as the application dose is within the detection sensitivity range of the measurement device used.

Next, based on the results of the measurement of the transmitted light obtained in step S06, the correlation between the erythema effective dose and the elapsed time is established by converting each spectral transmission spectrum of a temporal change (temporal change of the spectrum) into an erythema effective dose for a corresponding time (S07). Specifically, in a manner similar to step S03, a correlation such as correlation equations may be established based on the relationship between the minimal erythema doses obtained from plural temporal changes in the spectrum and the elapsed time, for example.

Next, based on the correlation such as correlation equations established in step S07, the erythema effective doses at predetermined times are calculated, and the correlation between the cumulative erythema effective dose and the elapsed time is established based on the calculation results (S08). It is noted that the settings disclosed in Japanese Patent No. 4365452 may be used in establishing the correlations in steps S07 and S08, for example. However, the present invention is not limited to such an example.

Next, based on the correlation between the cumulative erythema effective dose and the elapsed time obtained in step S08, an rSPF predictive value of the test sample is calculated (S09). It is noted that in step S09, the in vitro rSPF predictive value is calculated on the basis of the time it takes for the cumulative erythema effective dose, which is obtained through time integration based on the correlation, to reach 1 MED.

Also, in step S09, the calculated rSPF predictive value of the test sample may be corrected based on at least one of the in vitro rSPF predictive value obtained in step S05, the light source intensity, or the application dose at which a sample is applied to the skin substitute film. It is noted that the settings disclosed in Japanese Patent No. 4365452 may be used in step S09, for example. However, the present invention is not limited to such an example.

After step S09, an evaluation is performed based on processing results of the previous steps such as the calculation results and correction results (S10), a screen to be output by the output unit 32 is generated for displaying the evaluation result and other relevant information (S11), and the generated screen is output by the output unit 32 (S12).

<Light Source Used in the Present Embodiment>

Figure 5:
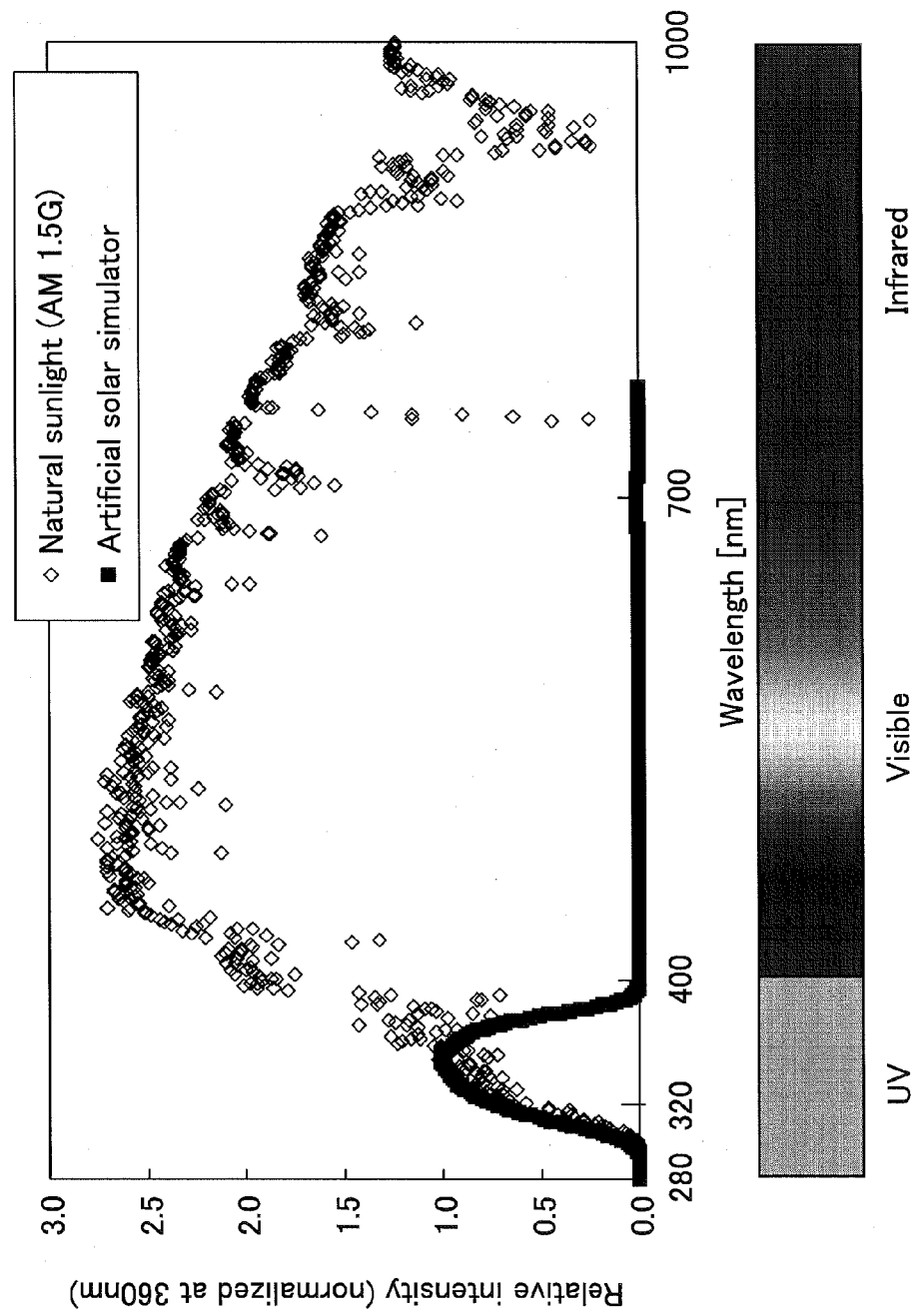
FIG. 5 is a graph illustrating exemplary light source spectrums.

In the following, light sources used in the present embodiment are described. FIG. 5 is a graph illustrating exemplary light source spectrums of light sources used in the present embodiment. It is noted that FIG. 5 shows differences in the spectral distributions of natural sunlight and an artificial solar simulator used for SPF testing. In FIG. 5, the horizontal axis represents the wavelength and the vertical axis represents the relative intensity.

As is shown in FIG. 5, the spectrums of natural sunlight and the artificial solar simulator used for SPF testing are actually quite different so that SPF values obtained using the artificial solar simulator do not accurately reflect the protective effect of a sample in real-life ultraviolet irradiation environments under real-life usage conditions of the user. Thus, merely providing SPF information for a product may be considered inadequate from a consumer protection standpoint. For example, when a user uses a product under an environment or conditions different from those under which the SPF values were obtained using a conventional in vitro SPF evaluation method or in vivo SPF evaluation method, the user may possibly sustain sunburns despite using the product.

Thus, in the present embodiment, a light source spectrum including the ultraviolet light range as well as the visible light range and the infrared light range that simulates the spectrum of natural sunlight is used in the evaluation.

In the following, specific examples of evaluations made in the evaluation process of the present embodiment are described.

<Material of Sample 1 and Method>

In the following, the material of the sample 1 used in the evaluation of the present embodiment is described. FIG. 6 is a table illustrating exemplary samples. In the example of FIG. 6, two types of sunscreen samples A and B were used in the evaluation. It is noted that upon conducting photostability evaluations (described below) on the samples A and B, sample A was determined to be photounstable, and sample B was determined to be photostable.

Figure 7A:
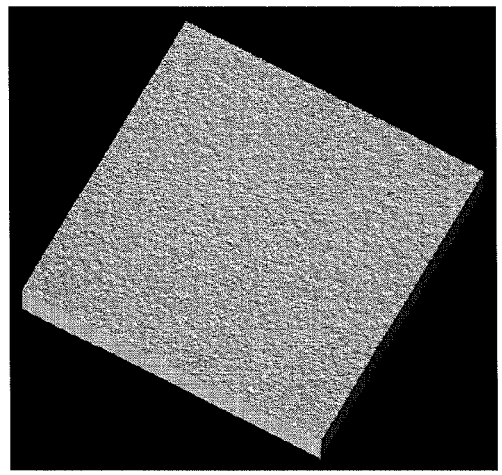
FIG. 7A is a first enlarged three-dimensional image of a portion of a substrate used in an evaluation according to an embodiment of the present invention.
Figure 7B:
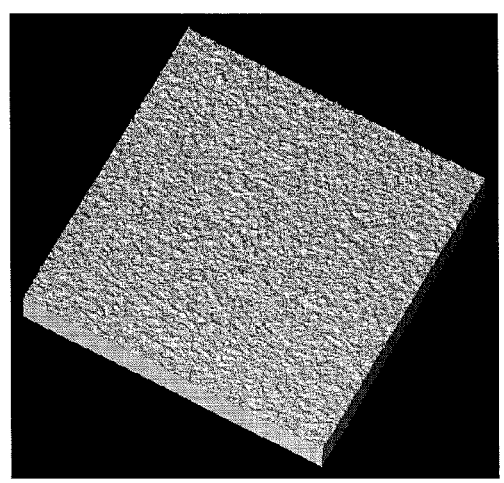
FIG. 7B is a second enlarged three-dimensional image of a portion of a substrate used in the evaluation.
Figure 7C:
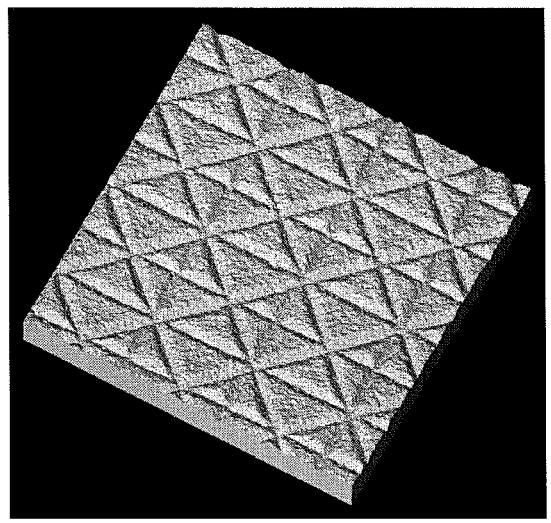
FIG. 7C is a third enlarged three-dimensional image of a portion of a substrate used in the evaluation.

FIGS. 7A-7C are enlarged three-dimensional images of portions of application substrates (PMMA (polymethylmethacrylate) plates) used in the present embodiment. Specifically, FIG. 7A shows an image of a Plexiglas (registered trademark) substrate; FIG. 7B shows an image of a HELIOPLATE HD6 substrate; and FIG. 7C shows an image of a Skin-Mimicking Substrate (SMS). It is noted that the above substrates each have recommended applications doses at which a sample is preferably applied; namely, the recommended application doses are 0.75 mg/cm$^2$ for FIG. 7A, 1.30 mg/cm$^2$ for FIG. 7B, and 2.00 mg/cm$^2$ for FIG. 7C.

Also, in the present example, the sunscreen samples were applied on the sides of the PMMA plates that are processed to have a certain roughness. Specifically, the calculated average surface roughness of the commercial Plexiglas substrate is arranged to be 2 μm, and its size is arranged to be approximately 50×50×2 mm. The calculated average surface roughness of the HELIOPLATE HD6 substrate is arranged to be 6 μm, and its size is arranged to be approximately 47×47×3 mm. The SMS simulating the surface of the skin is created through molding and is arranged to have a calculated average surface roughness of 17 μm and a size of approximately 50×50×0.8 mm. It is noted that the SMS has been developed as a simplified model of the skin surface configuration to reproduce the skin surface profile.

It is noted that surface profile measurements were conducted using a three-dimensional confocal microscope (i.e., HD100D by Lasertec Corporation). Also, the sample application doses were checked by measuring changes in the absorbance spectrum of sample A within a range from approximately 0.75 mg/cm$^2$ to approximately 2.00 mg/cm$^2$.

Also, in the present example, the fingertips were used to spread the sample evenly across the surfaces of the substrates shown in FIGS. 7A-7C. Further, three substrates were used for evaluating each sunscreen sample product.

<In Vivo SPF Evaluation>

In the present example, in vivo SPF evaluations were performed based on the above-described International SPF Test Method (CTFASA/COLIPA/JCIA/CTFA: May 2006), for example. The evaluations were all performed using Model 601-300 W Multiport (registered trademark) UV Solar Simulator (by Solar Light Company Inc.) at an intensity around 2 MED/min.

<Photostability Evaluation>

In the present example, evaluations of the transmitted light spectrums of the sunscreen samples applied on the substrates were conducted using the U-4100 spectrophotometer (by Hitachi High-Technologies Corporation). Also, the LC8 L9566 light source (by Hamamatsu Photonics K.K.) having a suitable filter combination was used as the artificial solar simulator to perform the photostability evaluation.

The sunscreen samples on the substrates were continuously exposed to light from the light source and their transmission spectrums were continuously monitored to evaluate their photostability.

The UV light source was adjusted to irradiate light at different intensities within a range from 0.05 MED/min (0.105 SED/min) to 4 MED/min (8.4 SED/min) using the PMA-2100 radiometer (by Solar Light Company Inc.). It is noted that light was continuously irradiated, and the light irradiation and transmission spectrum measurements were conducted on the same region. In the present example, a sample having an absorbance that decreases upon receiving light irradiation is deemed to be a photounstable sample, and a sample having a constant absorbance is deemed to be a photostable sample.

<Transmission Spectrum Measurement Using Evaluation Apparatus 10>

In evaluating samples using the evaluation apparatus 10 shown in FIG. 1, a xenon lamp with a filter for simulating an artificial solar simulator used in an in vivo SPF measurement method was used as a variable light source.

The intensity of the UV light source was adjusted using the PMA-2100 radiometer to 2 MED/min (4.2 SED/min), the intensity being the same as that used in the in vivo SPF testing). Such a system was used for in vitro evaluation of real-life SPF (rSPF).

<In Vitro SPF Algorithm>

Next, using the evaluation apparatus 10, the transmission spectrums of light having a wavelength range of 290-400 nm through sunscreen applied at various application doses on the PMMA substrates were measured. It is noted that the amount of UV light obtained from the transmission spectrum during light irradiation was monitored at the same location as that where photodegradation was continuously monitored through transmission measurement.

Then, relative erythema effective doses were determined from the transmission spectrums using the CIE-1987 erythema action spectrum. Also, the cumulative relative erythema effectiveness (CREE), which is a cumulative value of erythema effective doses weighted by the erythema action spectrum, was determined by the sum total of the relative erythema effective doses based on the transmission spectrums.

The endpoint of the algorithm for evaluating the rSPF was arranged to be at a point where the CREE reaches a value equivalent to 1 MED (2.1 SED). It is noted that this value is the same as the value used in evaluating an erythema reaction using an in vivo SPF determination method.

<Evaluation Results>

In the following, evaluation results obtained in the present embodiment are described. It is noted that the evaluation results may be obtained by the evaluation unit 37, and screens displaying the evaluations results may be generated by the screen generating unit 38 and output by the output unit 32.

Figure 8:
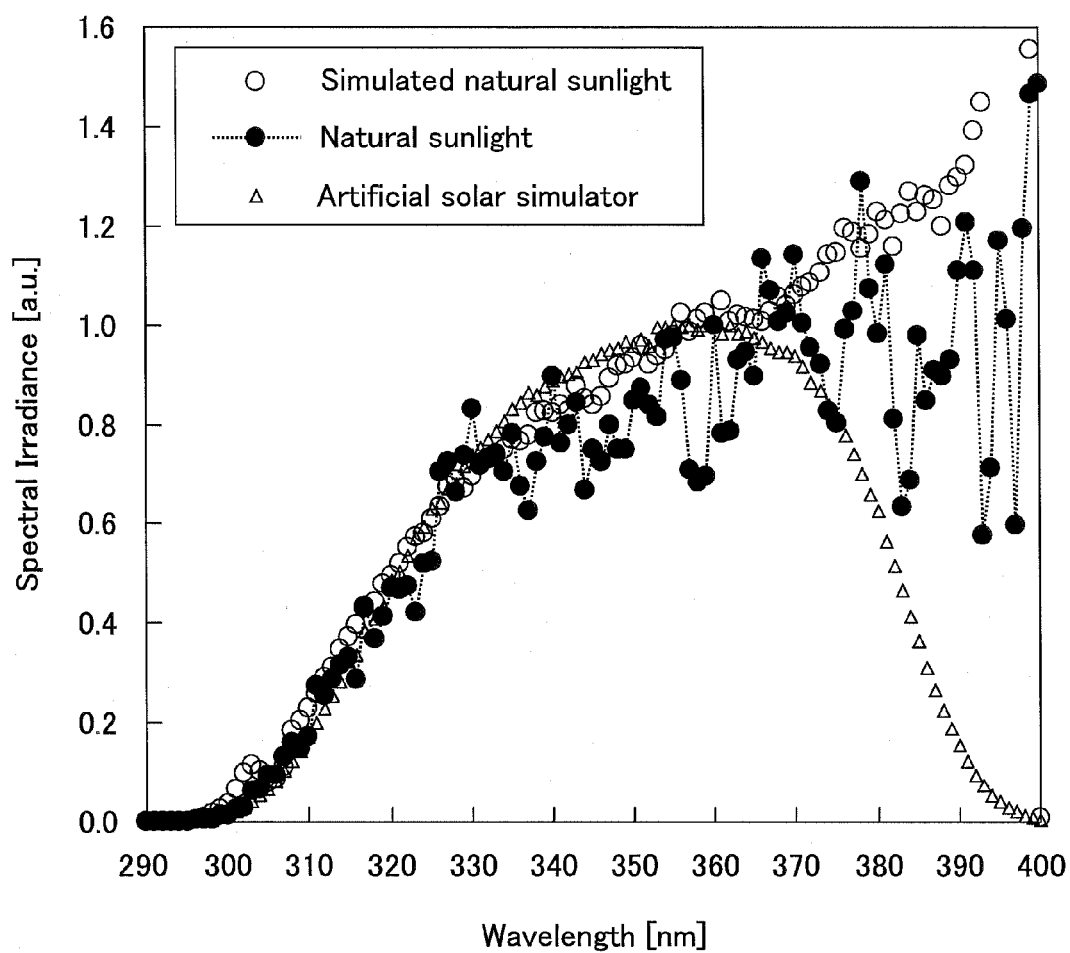
FIG. 8 is a graph illustrating light source spectrums in relation to the wavelength.

FIG. 8 is a graph representing light source spectrums in relation to the wavelength. That is, FIG. 8 compares the spectrums of the artificial solar simulator, simulated natural sunlight, and natural sunlight (normalized at 360 nm).

In FIG. 8, the simulated natural sunlight was re-created by adjusting the filter combination. Also, the spectrum of the artificial solar simulator was adjusted to match the acceptable range of the CREE (cumulative relative erythema effectiveness) for sunlight in the UV range. The spectrum of the simulated natural sunlight differs from the spectrum of the artificial solar simulator generally used in in vivo SPF testing from the wavelength around 370 nm and above.

<Absorbance Spectrum>

Figure 9:
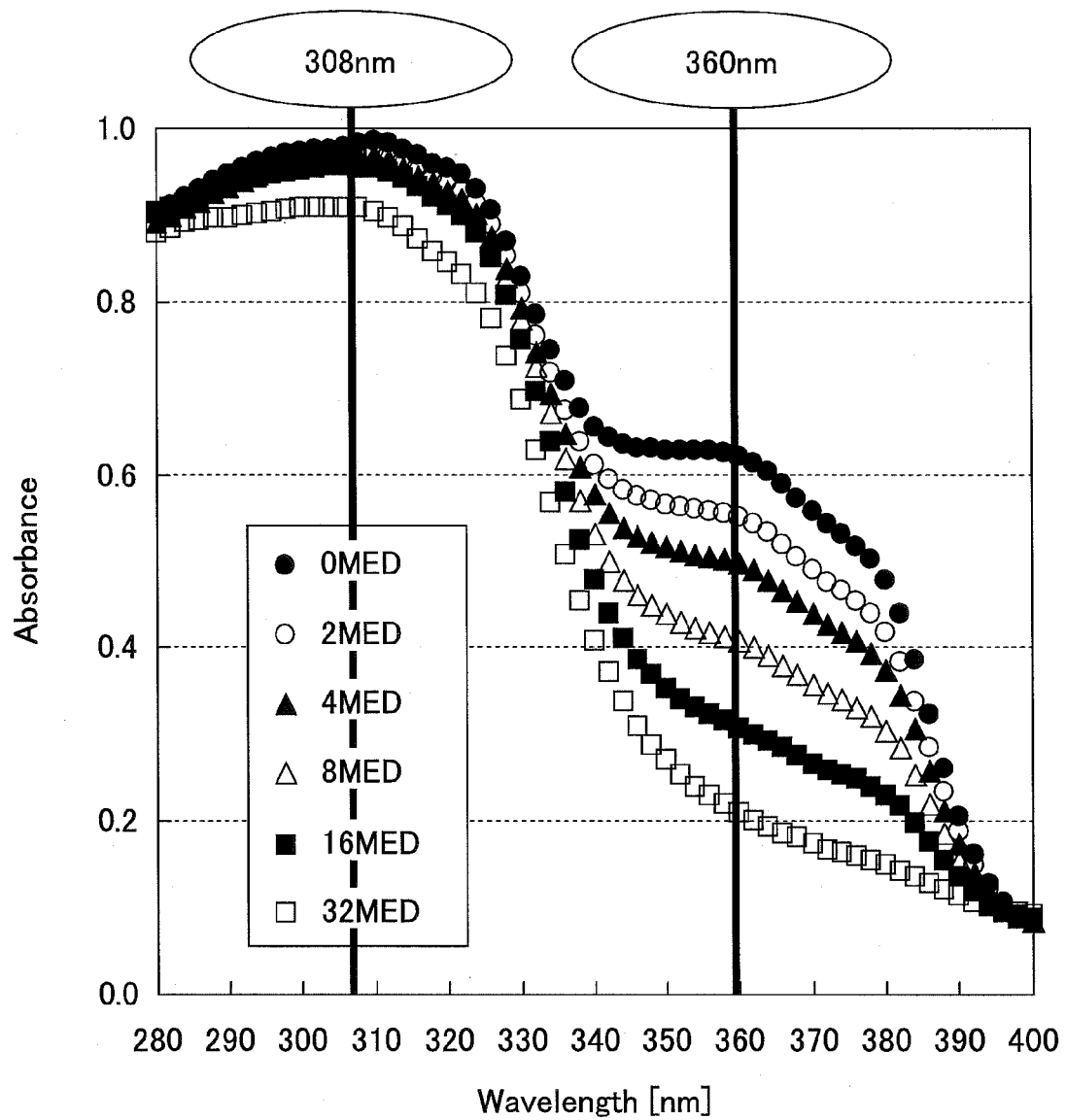
FIG. 9 is a graph illustrating exemplary evaluation results of absorbance spectrums indicating photodegradation.

FIG. 9 is a graph illustrating exemplary evaluation results of absorbance spectrums indicating photodegradation. The evaluation results of FIG. 9 include the spectrum change of the photounstable sample A upon being exposed to the simulated natural sunlight at a light source intensity of 2 MED/min.

In FIG. 9, a decrease in absorbance occurs at wavelengths 308 nm and 360 nm, for example. Further, upon comparing the two, the decrease in absorbance is greater at 360 nm than at 308 nm. This evaluation result indicates that photodegradation of UVB and UVA absorbing agents contained in the sample A occurs upon being exposed to light.

<Other Examples of Photodegradation>

Figure 10A:
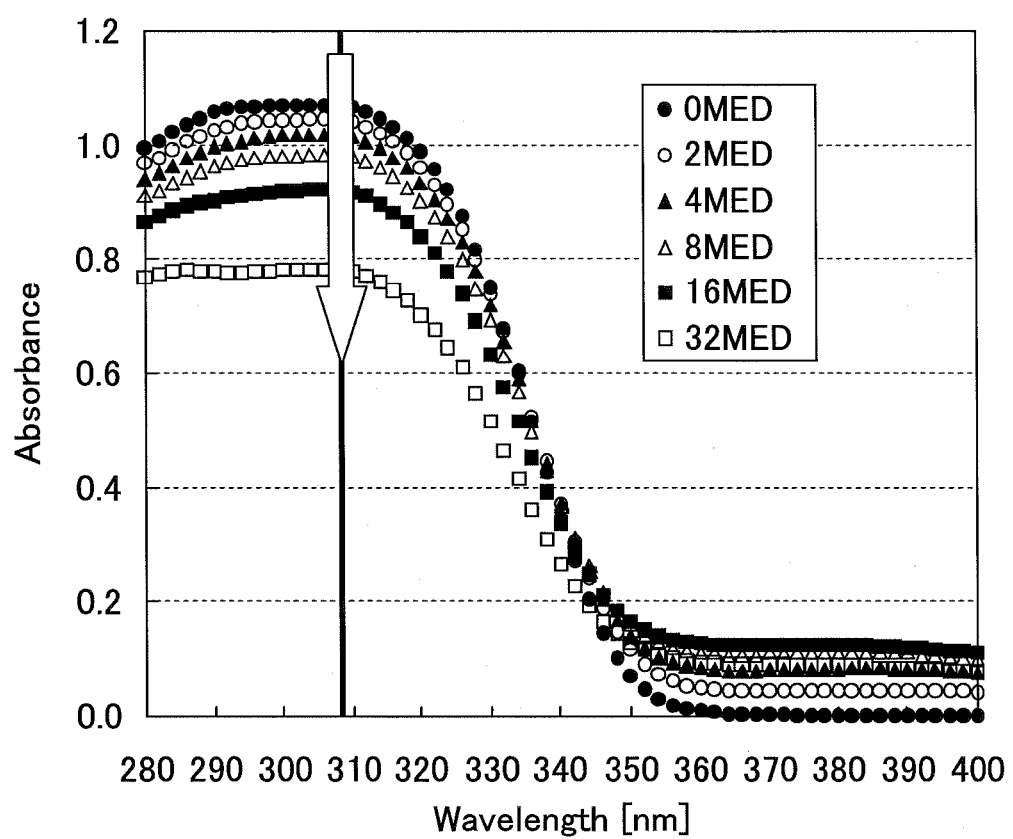
FIG. 10A is a graph illustrating another example of photodegradation.
Figure 10B:
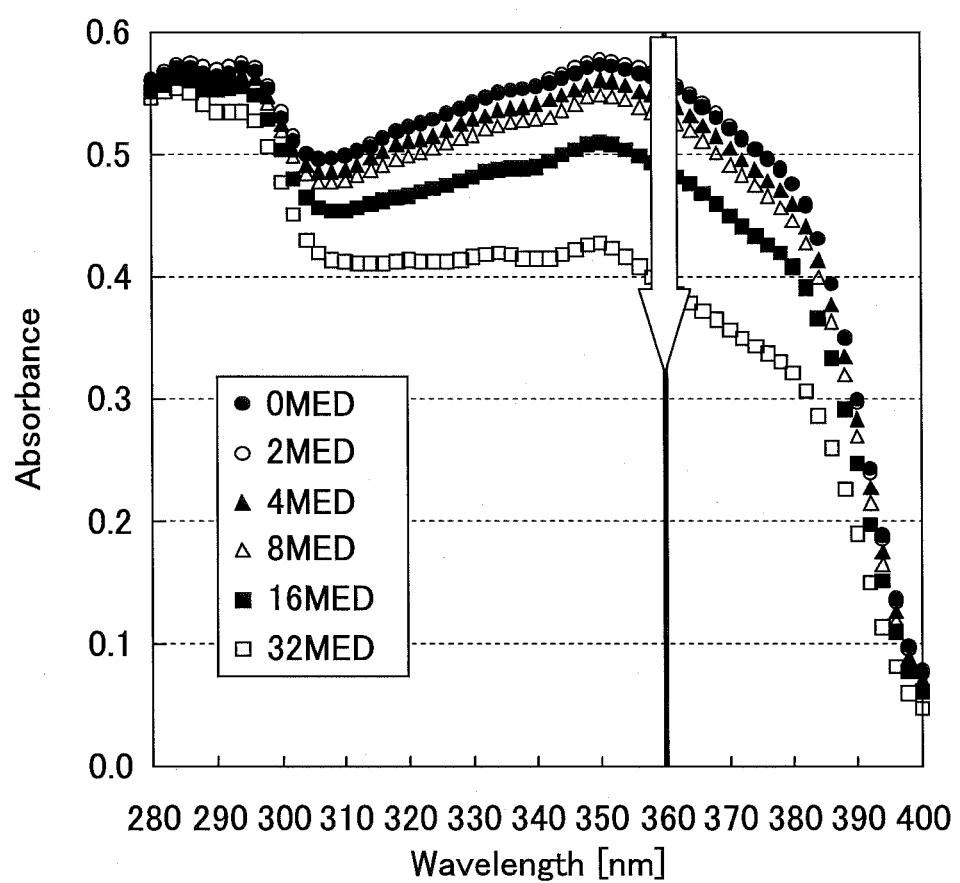
FIG. 10B is a graph illustrating another example of photodegradation.

FIG. 9 illustrates an example where ethylhexyl methoxyciannamate and butyl methoxydibenzoyl methane are included as the UV-absorbing agents susceptible to photodegradation. FIGS. 10A and 10B illustrate other examples indicating photodegradation. Specifically, FIG. 10A illustrates an example where ethylhexyl methoxycinnamate is included as the UV-absorbing agent susceptible to photodegradation; and FIG. 10B illustrates an example where butyl methoxydibenzoyl methane is included as the UV-absorbing agent susceptible to photodegradation. As can be appreciated from FIGS. 9, 10A, and 10B, the UV-absorbing agents have different photodegradation characteristics.

That is, there are certain organic ultraviolet light absorbents included in sunscreen products that are susceptible to photodegradation upon being exposed to ultraviolet light. Photodegradation is basically the degradation of the ultraviolet protective capacity of the UV-absorbing agent and may occur through simple destruction of the UV-absorbing agent or through isomerization of the UV-absorbing agent upon being exposed to ultraviolet light, for example.

Representative UV-absorbing agents that are susceptible to photodegradation upon ultraviolet light exposure include: (1) ethylhexyl methoxycinnamate (308 nm); and (2) butyl methoxydibenzoyl methane (360 nm) (the numeric values within the parentheses indicate the maximum absorption wavelengths). It is noted that FIGS. 10A and 10B respectively illustrate examples of photodegradation when (1) is included and when (2) is included. FIG. 9 illustrates an example of photodegradation when both (1) and (2) are included.

As can be appreciated from the above examples, upon being exposed to ultraviolet light, a decrease in absorbance; i.e., degradation of the ultraviolet protective capacity, occurs around the maximum absorbance wavelength of each of the UV-absorbing agents. Further, photodegradation with a different degradation pattern may occur when a UV-absorbing agent other than (1) or (2) that is also susceptible to photodegradation is included.

Figure 11:
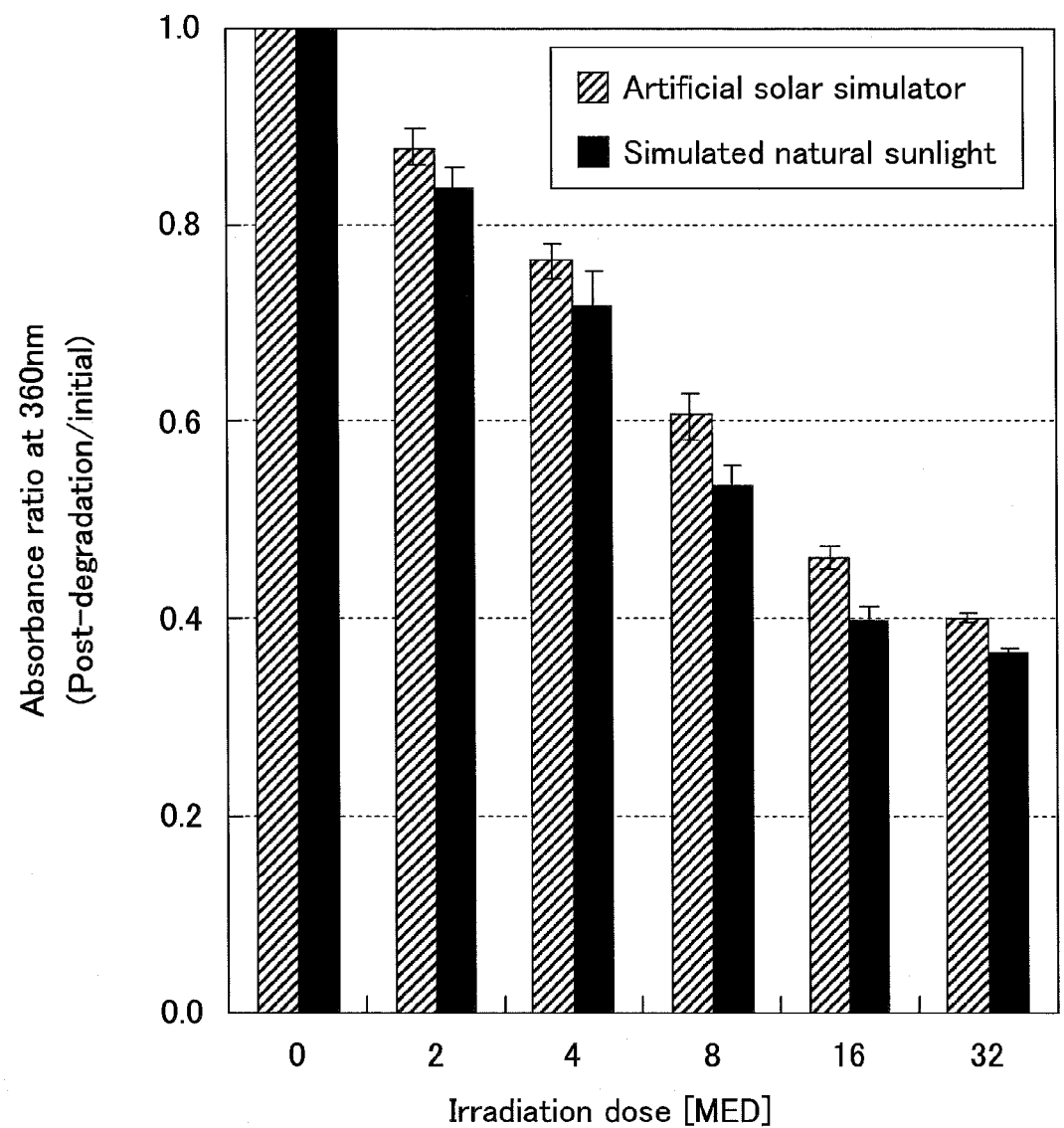
FIG. 11 is a graph illustrating differences in the absorbance decrease rates of a photounstable sample at 360 nm when being exposed to light from an artificial solar simulator and when being exposed to simulated natural sunlight.

FIG. 11 is a graph illustrating differences in the absorbance decrease rates of the photounstable sample A upon being exposed to light at a light intensity of 2 MED/min when the artificial solar simulator is used and when the simulated natural sunlight is used. Although photodegradation is apparent in both cases, the photodegradation is even more conspicuous in the measurements obtained using the simulated natural sunlight compared to the case of using the artificial solar simulator. These results indicate that photodegradation of a sample is dependent on the light source spectrum.

Further, the photostability of sunscreen was tested using the three different types of substrates. These tests were conducted using the recommended sample application doses for the respective substrates. That is, samples of the sunscreen were applied on the SMS, the HD6 substrate, and the Plexiglas substrate at approximately 2.00 mg/cm$^2$, approximately 1.30 mg/cm$^2$, and approximately 0.75 mg/cm$^2$, respectively. As is described above in connection with FIG. 9, the photounstable sample A has two main maximum absorption wavelengths at approximately 308 nm and approximately 360 nm (corresponding to the characteristics of the UV-absorbing agents included therein).

Figure 12A:
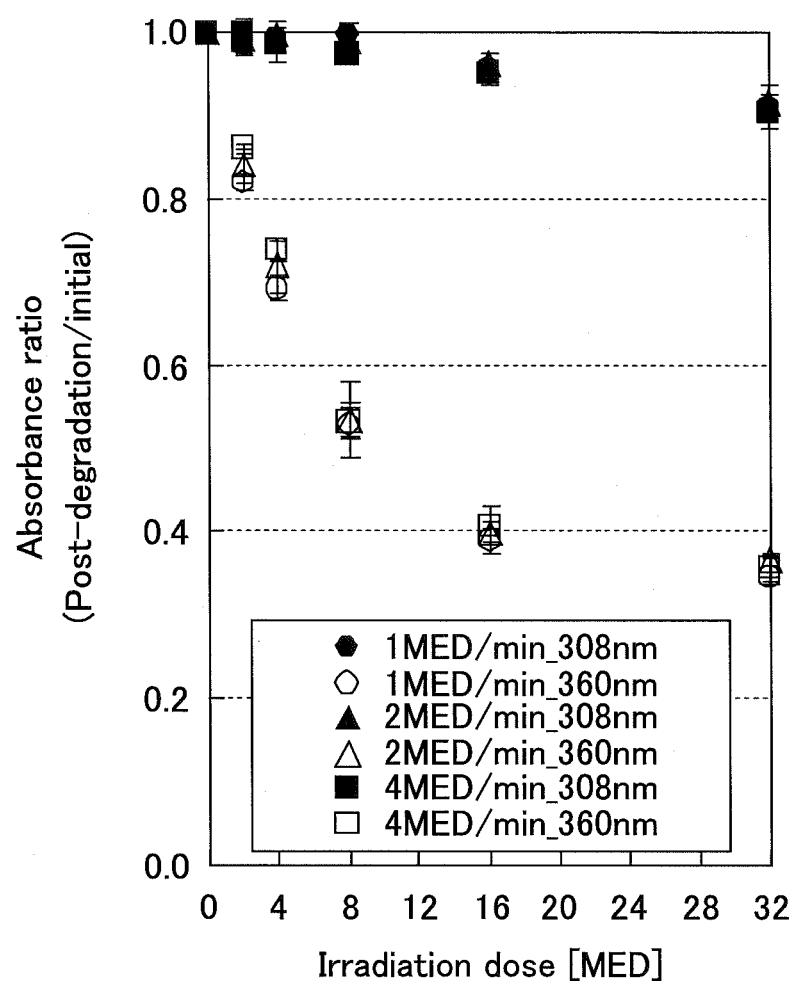
FIG. 12A is a graph illustrating photodegradation occurring in the photounstable sample applied to a skin-mimicking substrate upon being exposed to simulated natural light.
Figure 12B:
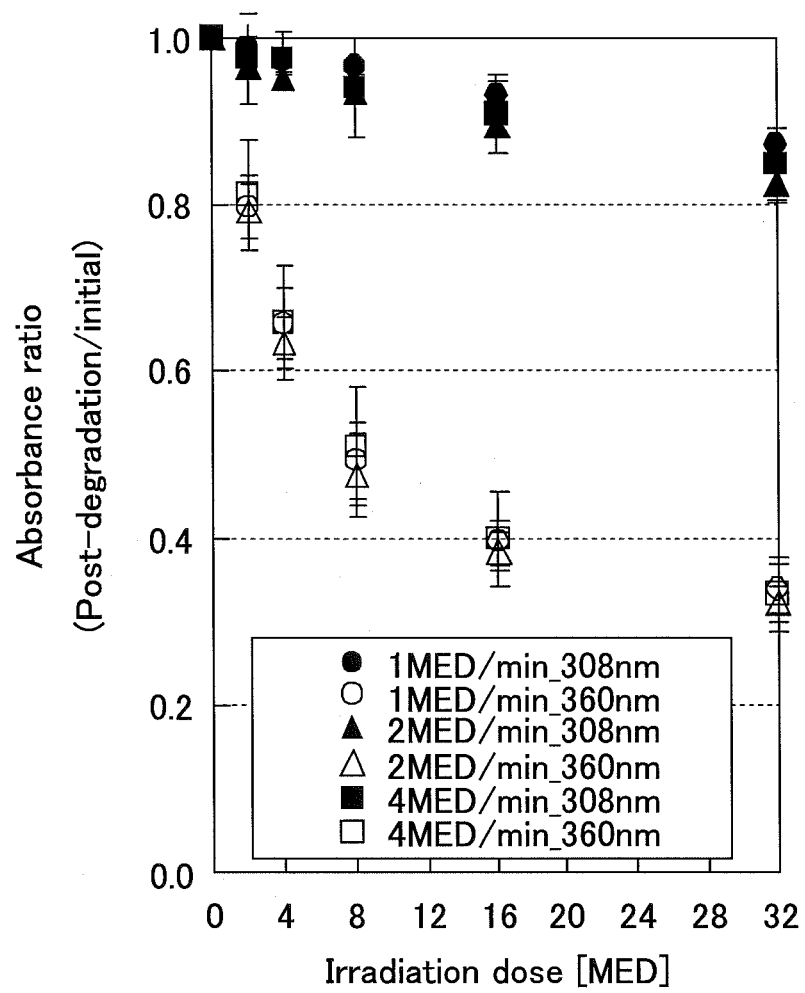
FIG. 12B is a graph illustrating photodegradation occurring in the photounstable sample applied to a HD6 substrate upon being exposed to simulated natural light.
Figure 12C:
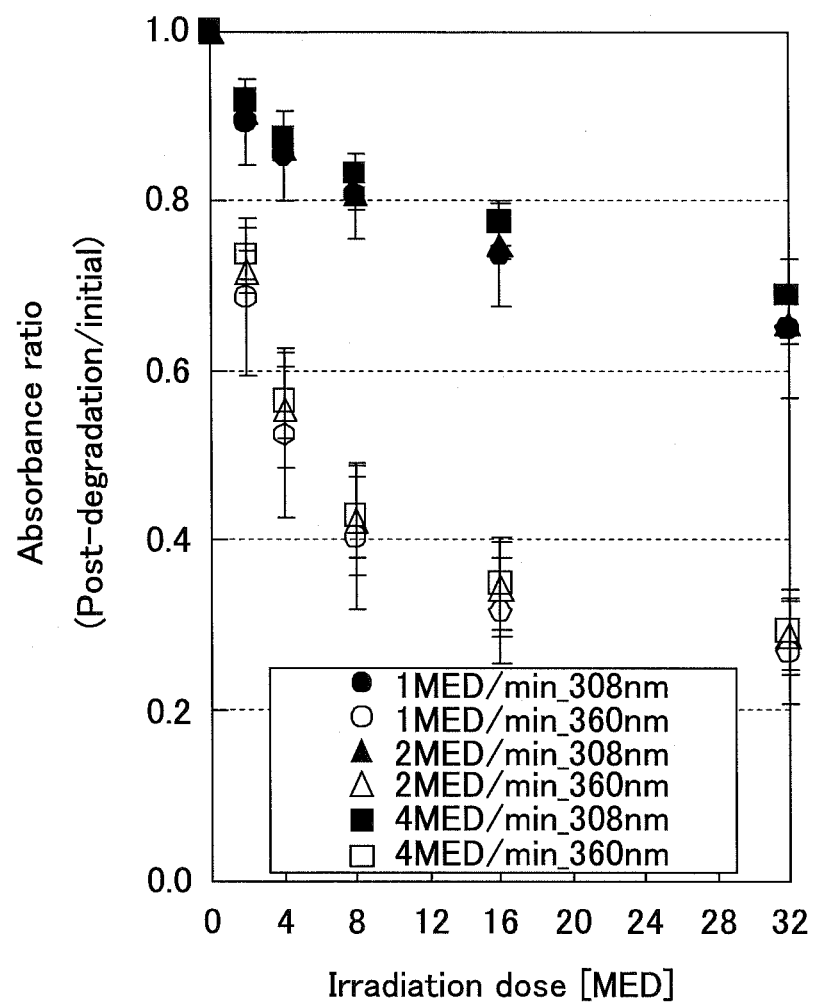
FIG. 12C is a graph illustrating photodegradation occurring in the photounstable sample applied to a Plexiglas substrate upon being exposed to simulated natural light.

FIGS. 12A-12C are graphs illustrating the photodegradation of the photounstable sample A applied on the three types of substrates upon being exposed to the simulated natural sunlight. Specifically, FIGS. 12A-12C indicate the impact of the irradiation intensity on the photodegradation of the sample A applied on the three substrates (where FIG. 12A illustrates the photodegradation of the SMS, FIG. 12B illustrates the photodegradation of the HD6 substrate, and FIG. 12C illustrates the photodegradation of the Plexiglas substrate). It is noted that the error bars shown in FIGS. 12A-12C represent standard deviations.

Also, it is noted that in FIG. 12A, the plate roughness is arranged to be approximately 17 μm and the sample application dose is arranged to be approximately 2.00 mg/cm$^2$; in FIG. 12B, the plate roughness is arranged to be approximately 6 μm and the sample application dose is arranged to be approximately 1.30 mg/cm$^2$; and in FIG. 12C, the plate roughness is arranged to be approximately 2 μm and the sample application dose is arranged to be approximately 0.75 mg/cm$^2$.

The measurement results of FIGS. 12A-12c indicate that photodegradation of the sample is dependent on the type of substrate used and the sample application dose. Also, the absorbance change ratios (post-degradation/initial) indicate that the change in absorbance is most conspicuous when Plexiglas is used and the sample application dose is the lowest.

That is, FIGS. 12A-12C indicate that the photodegradations may vary depending on the substrate (with varying application doses).

Further, the photodegradations were similar when the irradiation intensity was within a range from 1 MED/min to 4 MED/min. From the above, it may be determined that for the sample A, the reciprocity law applies within this intensity range.

Figure 13:
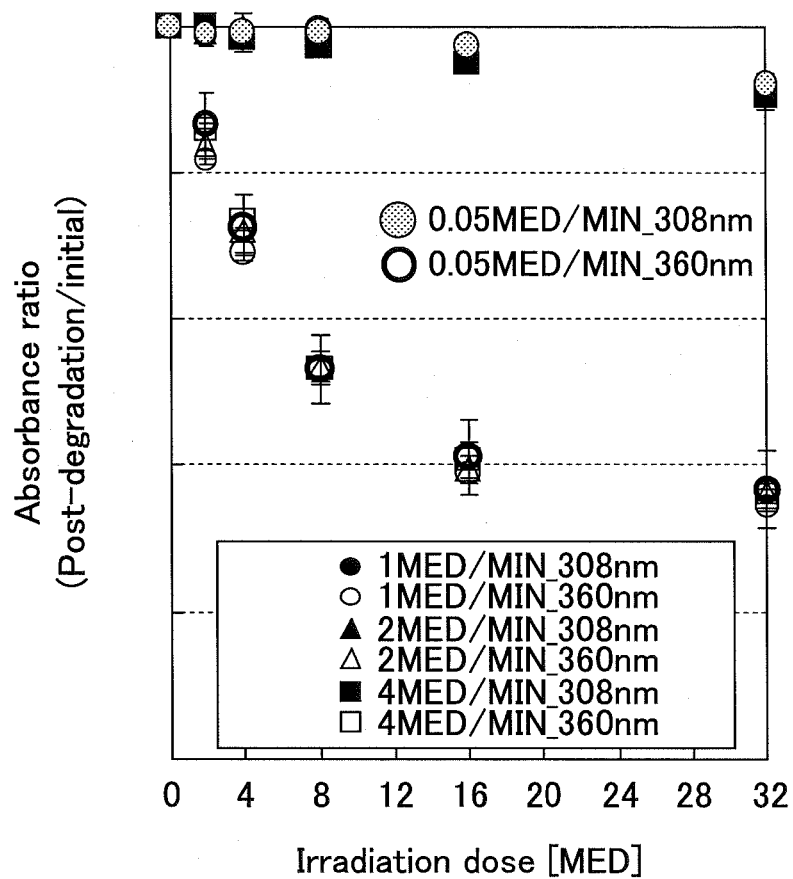
FIG. 13 is graph illustrating exemplary photodegradation characteristics of the photounstable sample applied to the skin-mimicking substrate upon being exposed to light within an intensity range of 0.05 MED/min (approximately equal to the intensity of actual sunlight of midsummer in Japan) to 4 MED/min.

FIG. 13 is a graph illustrating an exemplary degradation behavior of the sample A applied on the SMS upon being exposed to light within an intensity range of 0.05 MED/min (approximately equal to the intensity of natural sunlight of midsummer in Japan) to 4 MED/min.

As is shown in FIG. 13, the degradation behavior of the sample A upon being exposed to light with an intensity of 0.05 MED/min, which is approximately equal to the intensity of natural sunlight of midsummer in Japan, is approximately the same as the degradation behavior when the light intensity is within the range of 1-4 MED/min. This indicates that the reciprocity law applies to the sample A within this intensity range.

In other words, in evaluating the in vitro rSPF in the present embodiment, the same predictive value will be obtained regardless of the light source intensity as long as the light source intensity is within the range of 0.05-4 MED/min. Thus, the light source intensity may be increased to reduce the measurement time, for example. That is, FIG. 13 indicates that the in vitro rSPF at the intensity of actual sunlight (0.05 MED/min) may be accurately estimated using a light intensity that is stronger than that of the actual sunlight.

Figure 14:
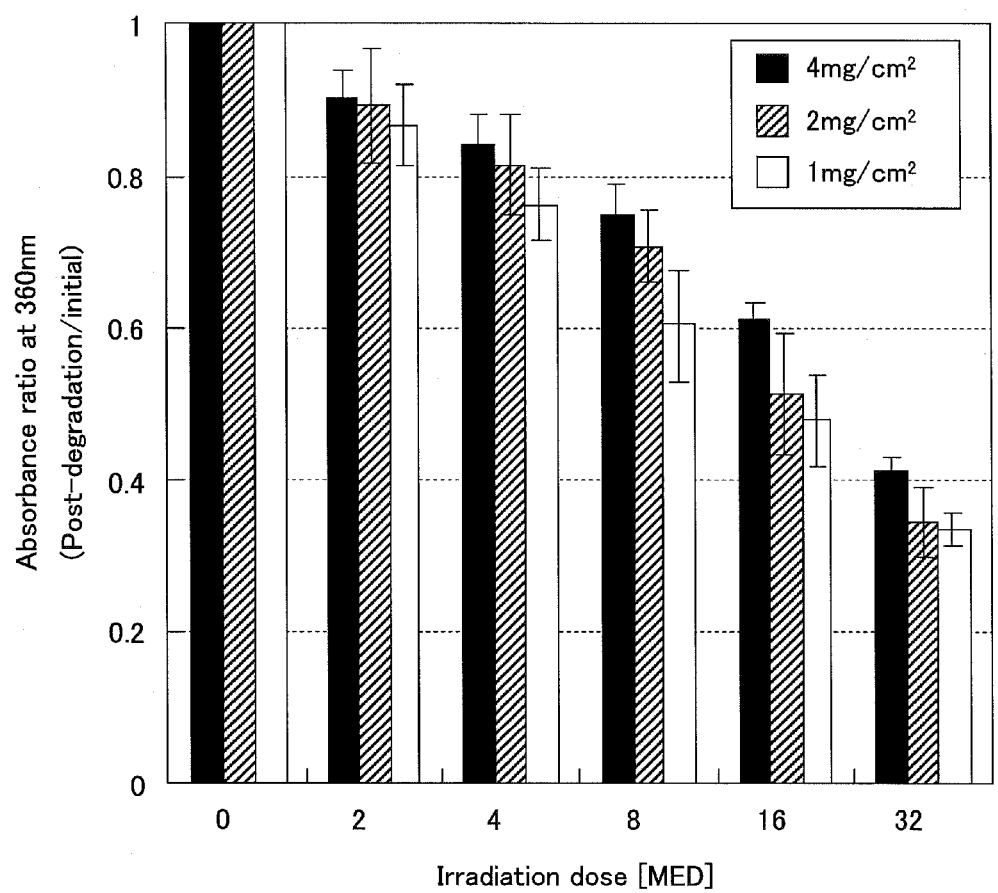
FIG. 14 is a graph illustrating differences in the absorbance decrease rates of the photounstable sample at 360 nm when applying the sample at differing sample application doses.

FIG. 14 is a graph illustrating differences in the absorbance decrease rates of the photounstable sample A at 360 nm when the sample A is applied at different application doses on the SMS. It is noted that the error bars shown in FIG. 14 represent standard deviations. FIG. 14 represents an evaluation of the impact of the sample application dose on the absorbance change ratio (post-degradation/initial) at 360 nm when using the SMS as the substrate.

As can be appreciated from FIG. 14, photodegradation of the sample is dependent on the sample application dose. In sum, evaluation factors affecting photodegradation of the sample include the light source spectrum, the sample application substrate, and the sample application dose. Accordingly, it is important to take these factors into consideration in the in vitro rSPF evaluation.

<Evaluation of Application Reproducibility of the Sample Application Substrates>

Figure 15A:
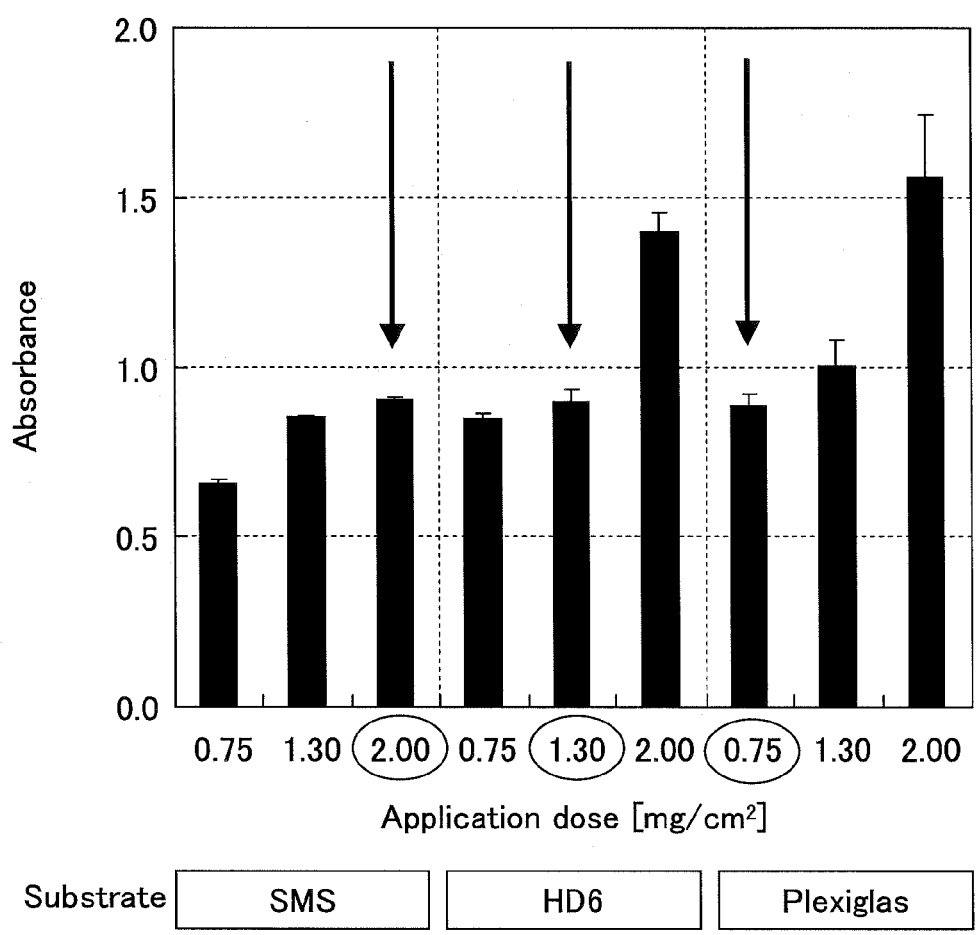
FIG. 15A is a first graph illustrating an exemplary evaluation of the reproducibility of the application of the photounstable sample applied on the three different substrates at various application doses based on the absorbance of the sample at 308 nm.
Figure 15B:
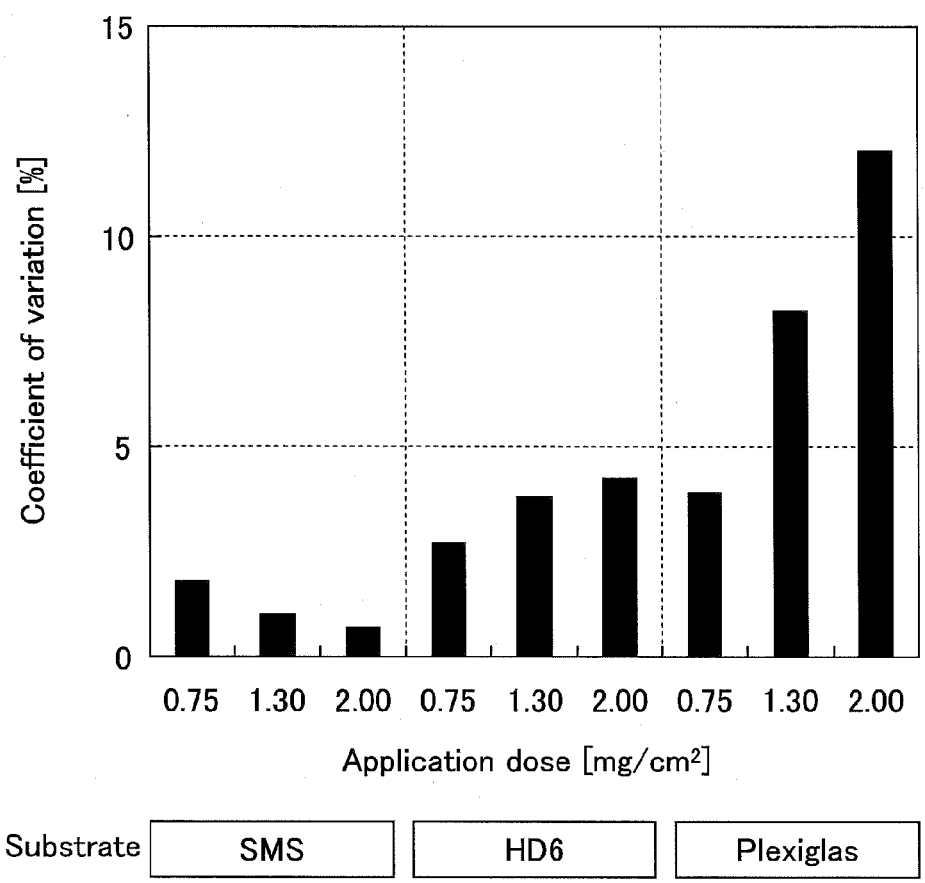
FIG. 15B is a second graph illustrating the exemplary evaluation of the reproducibility of the application of the photounstable sample applied on the three different substrates at various application doses based on the absorbance of the sample at 308 nm.

In the following, tests conducted for comparing the sample application reproducibility of the various sample application substrates are described. FIGS. 15A and 15B illustrate exemplary evaluation results of the reproducibility of application of the sample A applied at various application doses on the three substrates based on the absorbance of the sample at 308 nm. The error bars shown in FIGS. 15A and 15B represent standard deviations.

It is noted that these evaluations were conducted to select a suitable substrate for rSPF evaluation of the sunscreen sample. To this end, absorbance measurements were conducted three times for each of the three different substrates.

FIGS. 15A and 15B indicate that the SMS has the most suitable characteristics for the rSPF evaluation because it has high application reproducibility and allows application of the sample at various application doses ranging from 0.75 mg/cm$^2$, which is assumed to be the actual application dose at which the sample is applied by a user, to 2.00 mg/cm$^2$. Thus, the SMS was selected as the substrate to be used in the rSPF evaluation. It is noted that the absorbance values from application of the sample on the different substrates at their corresponding recommended sample application doses (SMS: 2.00 mg/cm$^2$; HD6: 1.30 mg/cm$^2$; and Plexiglas: 0.75 mg/cm$^2$) were substantially the same.

<In Vitro SPF Evaluation>

Figure 16A:
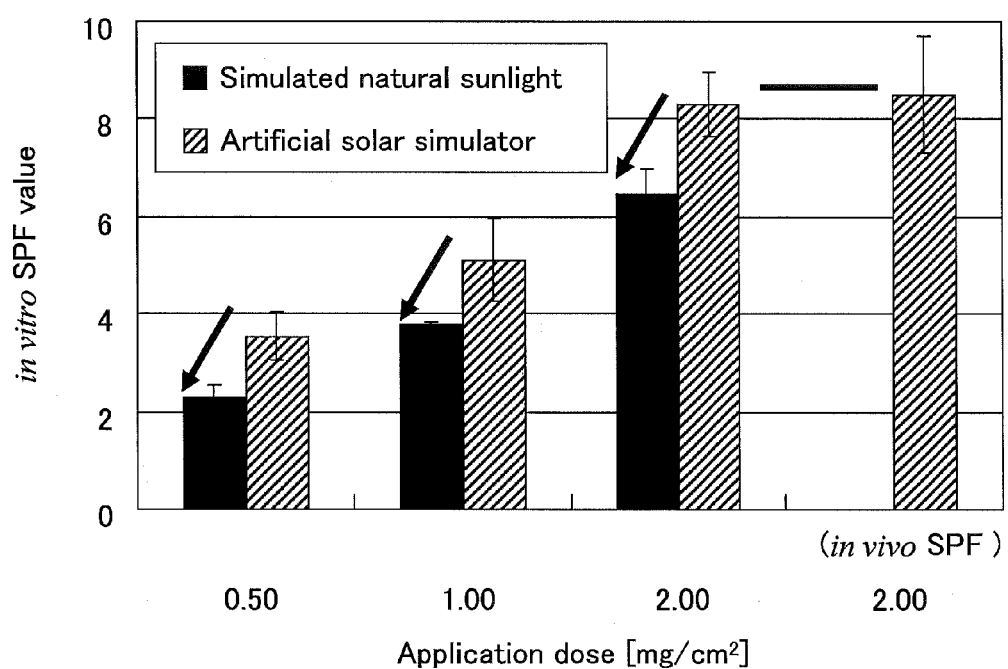
FIG. 16A is a graph illustrating an impact of the light source spectrum on in vitro SPF values obtained for the photounstable sample at various application doses.
Figure 16B:
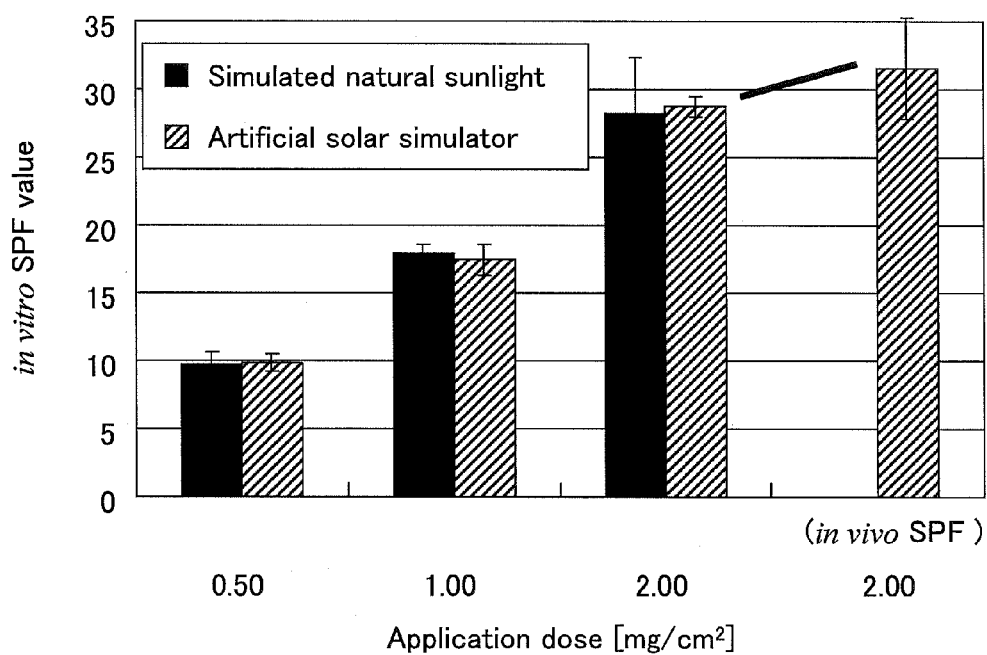
FIG. 16B is a graph illustrating an impact of the light source spectrum on in vitro SPF values obtained for a photostable sample at various application doses.

FIGS. 16A and 16B are graphs illustrating the impact of the light source spectrum on the in vitro SPF values obtained for the photounstable sample A and the photostable sample B at various application doses.

FIG. 16A indicates that the in vivo SPF value for the sample A is 8.5±1.2, and FIG. 16B indicates that the in vivo SPF value for the sample B is 31.5±3.7. Also, the error bars shown in FIGS. 16A and 16B represent standard deviations.

Evaluating the impact of the application dose and the light source spectrum on the in vitro SPF values of a photostable sample using the samples A and B, in vitro SPF values could be estimated using the SMS as the substrate at application doses ranging from 0.50 mg/cm$^2$, which reproduces the actual application dose, to 2.00 mg/cm$^2$. As shown in FIGS. 16A and 16B, the in vitro SPF values are dependent on the application dose.

In the case of using the artificial solar simulator (used for in vivo SPF evaluation) as the light source, in vitro SPF values equivalent to the corresponding in vivo SPF values could be obtained for both samples A and B by applying these samples on the SMS at an application dose of 2.00 mg/cm$^2$. Further, different results may be obtained by using other different light source spectrums.

That is, in obtaining the in vitro SPF values for the photounstable sample A, the values obtained when using the simulated natural sunlight as the light source are lower compared to the values obtained when using the artificial solar simulator as the light source. These results represent photodegradation characteristics similar to that illustrated in FIG. 11. That is, photodegradation of the sample A is accelerated when the simulated natural sunlight is used. On the other hand, because the photostable sample B is not affected by the light irradiation by the light source, the same in vitro SPF values were obtained for sample B even when different light sources were used.

<Using Different Sample Base Materials>

In the following, evaluation results obtained from using different sample bases are described. FIG. 17 is a table illustrating the in vitro rSPF values obtained for three different types of sample bases (samples X, Y, and Z) applied on three different regions. Specifically, FIG. 17 shows measurement results of simulated sample applications on the cheek, arm, and back, as application regions (applied regions) with respect to panels A, B, and C. It is noted that the "actual average application dose" refers to the average application dose obtained from actually applying the sample on a 5×5 cm application region on five occasions.

As shown in FIG. 17, in order to simulate actual usage conditions of the samples (X, Y, and Z) used in the present embodiment, the average roughness of the skin substitute film may be adjusted based on the average roughness data of the skin, for example.

In the present embodiment, a plate having a simplified surface profile based on the configuration of a skin replica is used, and a sample is applied at an "actual sample application dose" in the evaluation using a "sample application method" that is used in real-life by actual users to estimate the ultraviolet protection effect of the sample in the form of numeric values.

For example, a SMS having a surface roughness based on the skin surface roughness of a specific region such as the back region may be used in the present embodiment. However, the present invention is not limited to such an example. That is, because the skin surface roughness may be different for each measurement region (e.g., cheek, aim, or back), the surface roughness may be adjusted according to the corresponding measurement region.

For example, a sunscreen application region is not limited to the back region (roughness approximately 25 µm) but also includes regions such as the cheek (roughness approximately 9 µm) and the neck (roughness approximately 17 µm). Thus, different types of application plates may be selected according to the roughness of the application region of the skin. In this way, the corresponding rSPF value for the region may be accurately estimated, for example.

As can be appreciated, the roughness of the region on which the sample is applied and the application dose at which the sample is applied are important factors affecting the calculation of the rSPF predictive value. Accordingly, in the present embodiment, physical measurements are made based on such information so that the ultraviolet protection effect for each individual region may be accurately predicted.

<Summary of Evaluation Results>

Standardized SPF protocols exist for in vivo SPF measurement methods as exemplified by the above-described International SPF Test Method. The in vivo SPF test methods based on these protocols have been conducted for a long time.

However, in these standardized methods, for example, a solar simulator that cuts out visible light and infrared light included in natural sunlight is used as the light source so that the irradiated light is quite different from natural sunlight.

Because in vivo evaluation based on real-life usage environments and usage conditions cannot realistically be conducted using human test subjects due to the long sunlight irradiation time required to conduct such tests, there has been no adequate disclosures on techniques for conducting such tests. According to an aspect of the present embodiment, an in vitro evaluation method is provided that enables reliable prediction of rSPF values through physical measurement without relying on human test subjects.

That is, in the present embodiment, the impact of the light source spectrum on the spectral changes of the photounstable sample A is taken into consideration, and the impact of light having a wavelength range of 370 nm and above on the photodegradation of the photounstable sample A is recognized. By using an algorithm that continuously measures the transmission spectrum of a sample while taking into account the photostability evaluation of the sample, in vitro SPF values may be accurately predicted regardless of the photostability of the sunscreen sample.

Also, as shown in FIGS. 12A-12C and 14, the photostablity of the sample A of depends on the application dose, and photodegradation of the sample A is accelerated as the application dose is decreased. This means that photodegradation of a sample has an impact on the ultraviolet protection effect evaluation of the sample. This also means that the photostability of the sample should be taken into account in evaluating the ultraviolet protection effect of the sample. Also, as can be appreciated from FIGS. 15A, 15B, 16A, and 16B, a SMS (PMMA plate) having a roughness equivalent to that of the skin is preferably used in the in vitro rSPF evaluation in view of its permissible application dose range and its high sample application reproducibility.

Further, it is noted that the rSPF value obtained for the sample A at an application dose of 1.00 mg/cm$^2$ using the artificial solar simulator is equal to less than half the in vivo SPF value of the sample A. As described above, a typical sunscreen application dose is generally believed to be within a range of 0.50-1.50 mg/cm$^2$. However, the SPF values indicated on sunscreen products are based on values obtained from applying the sunscreen at an application dose of 2.00 mg/cm$^2$. Thus, it should be understood that such SPF values are not absolute measures of the ultraviolet protection effect of the sunscreen under real-life usage environments and usage conditions. Based on the findings made in the present embodiment, the "rSPF" is preferably used as a practical means for ultraviolet protection. Also, predicting rSPF values under conditions reflecting the actual conditions of sunlight to which consumers are exposed and the actual sample application dose used by consumers may be important from a consumer protection standpoint. Based on the above evaluation results, evaluation of rSPF values according to the present embodiment may involve the following steps:

1. Determine typical sample application dose by user
2. Apply sample on a substrate simulating the skin (SMS) at the sample application dose determined above
3. Measure in vitro rSPF values under the following measurement conditions:
    (1) Use simulated natural sunlight as the light source spectrum
    (2) Adjust light source intensity to be within 1-4 MED/min
    (3) Arrange endpoint of algorithm to be at a point where the cumulative erythema effective dose reaches a value equivalent to 1 MED (minimal erythema dose) (i.e., in accordance with erythema reaction determination based on the in vivo SPF evaluation method).

Also, in the present embodiment, the light source intensity is preferably arranged to be approximately 0.001-20.0 MED/min, the sample application dose is preferably arranged to be approximately 0.01-10.0 mg/cm$^2$, and the calculated average roughness (Sa value) of the application plate is preferably arranged to be approximately 0.01-400 μm.

According to an aspect of the present invention, an ultraviolet protection effect of sunscreen against ultraviolet light irradiated under real-life environments under real-life usage conditions may be accurately evaluated. Also, by using a sensitive evaluation apparatus, photodegradation may be reflected in the prediction of the in vitro rSPF values. Further, the in vitro rSPF evaluation method according to the present embodiment enables a skin substrate film (SMS) having a surface configuration simulating that of the skin to reproduce ultraviolet light exposure on the skin having a sample such as sunscreen applied thereon at an actual sample application dose.

Further, the present invention is not limited to the embodiments described above, and numerous variations and modifications may be made without departing from the scope of the present invention.

The present application is based on and claims the benefit of priority of Japanese Patent Application No. 2010-209818 filed on Sep. 17, 2010, the entire contents of which are herein incorporated by reference.

DESCRIPTION OF THE REFERENCE NUMERALS 1 sample
10 evaluation apparatus
11 light source
12 power supply unit
13 filter
14 optical fiber
15 integrating sphere
16 stage
17 stage drive unit
18 optical chopper
19 monochromator (spectrometer)
20 UV-PMT (light detector)
21 PMT voltage controller
22 signal amplifier (Amp)
23 PC
31 input unit
32 output unit
33 storage unit
34 temporal change measurement unit
35 correlation setting unit
36 SPF predictive value calculation unit
37 evaluation unit
38 screen generation unit
39 control unit
41 input device
42 output device
43 drive device
44 auxiliary storage device
45 memory device
46 CPU
47 network connection device
48 recording medium

The invention claimed is:

1. An evaluation method for evaluating an ultraviolet protection effect of a measurement sample applied on a substrate, the evaluation method comprising:
- a first step of measuring, at predetermined wavelength intervals, a change over time of a spectral transmission spectrum of the measurement sample within a predetermined wavelength range of a waveform approximating a spectral waveform of actual sunlight by irradiating light from a light source that has a wavelength range of 200-1000 nm and includes ultraviolet light, visible light, and infrared light under a predetermined irradiation condition, and arranging the light to have a shape approximating the spectral waveform of actual sunlight using a filter;
- a second step of establishing, based on the change over time of the spectral transmission spectrum, a correlation between a light irradiation time and an erythema effective dose per unit time, which is obtained by dividing an erythema effective dose of the measurement sample by an erythema effective dose per 1 MED; and
- a third step of calculating an in vitro rSPF predictive value for the measurement sample on the basis of a time until a cumulative erythema effective dose, which is obtained through time integration based on the correlation, reaches 1 MED, the in vitro rSPF predictive value indicating a protection effect against ultraviolet light included in light from a solar light source irradiated under a real-life usage condition and a real-life usage environment for the measurement sample; wherein
- the real-life usage condition includes arranging an application dose range of the measurement sample applied on the substrate to 0.01-10.0 mg/cm2 and arranging a calculated average roughness (Sa value) range of the substrate to be 0.01-400 μm; and
- the real-life usage environment includes arranging an intensity range of the light source that irradiates the light to 0.001-20.0 MED/min.

2. An evaluation apparatus for evaluating an ultraviolet protection effect of a measurement sample applied on a substrate, the evaluation apparatus comprising:
- a temporal change measurement unit for measuring, at predetermined wavelength intervals, a change over time of a spectral transmission spectrum of the measurement sample within a predetermined wavelength range of a waveform approximating a spectral waveform of actual sunlight by irradiating light from a light source that has a wavelength range of 200-1000 nm and includes ultraviolet light, visible light, and infrared light under a predetermined irradiation condition, and arranging the light to have a shape approximating the spectral waveform of actual sunlight using a filter;
- a correlation setting unit for establishing, based on the change over time of the spectral transmission spectrum, a correlation between an irradiation time and an erythema effective dose per unit time, which is obtained by dividing an erythema effective dose of the measurement sample by an erythema effective dose per 1 MED; and
- a SPF predictive value calculation unit for calculating an in vitro rSPF predictive value for the measurement sample on the basis of a time until a cumulative erythema effective dose, which is obtained through time integration based on the correlation, reaches 1 MED, the in vitro rSPF predictive value indicating a protection effect against ultraviolet light included in light from a solar light source irradiated under a real-life usage condition and a real-life usage environment for the measurement sample; wherein
- the real-life usage condition includes arranging an application dose range of the measurement sample applied on the substrate to 0.01-10.0 mg/cm2 and arranging a calculated average roughness (Sa value) range of the substrate to be 0.01-400 μm; and
- the real-life usage environment includes arranging an intensity range of the light source that irradiates the light to 0.001-20.0 MED/min.

3. The evaluation apparatus as claimed in claim 2, wherein the temporal change measurement unit measures the change over time of the spectral transmission spectrum at arbitrary time intervals.

4. The evaluation apparatus as claimed in claim 2, wherein the temporal change measurement unit measures a change over time of the spectral transmission spectrum of the measurement sample caused by photodegradation.

5. The evaluation apparatus as claimed in claim 2, wherein the SPF predictive value calculation unit calculates the in vitro rSPF predictive value for the measurement sample on the basis of the time until the cumulative erythema effective dose reaches 1 MED; and corrects the calculated in vitro rSPF predictive value for the measurement sample using at least one of an in vitro rSPF predictive value for a reference sample that is evaluated beforehand, a light source intensity used to evaluate the reference sample, and a sample application dose of the reference sample.

6. A computer-readable medium storing an evaluation program for evaluating an ultraviolet protection effect of a measurement sample applied on a substrate, the evaluation program including a sequence of instructions, which when executed by a computer, cause the computer to perform:
- a first step of measuring, at predetermined wavelength intervals, a change over time of a spectral transmission spectrum of the measurement sample within a predetermined wavelength range of a waveform approximating a spectral waveform of actual sunlight by irradiating light from a light source that has a wavelength range of 200-1000 nm and includes ultraviolet light, visible light, and infrared light under a predetermined irradiation condition, and arranging the light to have a shape approximating the spectral waveform of actual sunlight using a filter;
- a second step of establishing, based on the change over time of the spectral transmission spectrum, a correlation between a light irradiation time and an erythema effective dose per unit time, which is obtained by dividing an erythema effective dose of the measurement sample by an erythema effective dose per 1 MED; and
- a third step of calculating an in vitro rSPF predictive value for the measurement sample on the basis of a time until a cumulative erythema effective dose, which is obtained through time integration based on the correlation, reaches 1 MED, the in vitro rSPF predictive value indicating a protection effect against ultraviolet light included in light from a solar light source irradiated under a real-life usage condition and a real-life usage environment for the measurement sample; wherein
- the real-life usage condition includes arranging an application dose range of the measurement sample applied on the substrate to 0.01-10.0 mg/cm2 and arranging a calculated average roughness (Sa value) range of the substrate to be 0.01-400 μm; and
- the real-life usage environment includes arranging an intensity range of the light source that irradiates the light to 0.001-20.0 MED/min.

* * * * *